US012133875B2

(12) United States Patent
Tsurumoto et al.

(10) Patent No.: US 12,133,875 B2
(45) Date of Patent: Nov. 5, 2024

(54) METHOD AND APPARATUS FOR TREATING POST-HARVEST PLANT

(71) Applicant: NICHIA CORPORATION, Anan (JP)

(72) Inventors: Tomohiro Tsurumoto, Yokohama (JP); Yasuo Fujikawa, Yokohama (JP); Takahiro Oyu, Herzliya (IL)

(73) Assignee: NICHIA CORPORATION, Anan (JP)

( * ) Notice: Subject to any disclaimer, the term of this patent is extended or adjusted under 35 U.S.C. 154(b) by 419 days.

(21) Appl. No.: 17/656,414

(22) Filed: Mar. 24, 2022

(65) Prior Publication Data

US 2022/0313765 A1 Oct. 6, 2022

(30) Foreign Application Priority Data

Mar. 25, 2021 (JP) .................................. 2021-051885

(51) Int. Cl.
 *A61K 36/185* (2006.01)
(52) U.S. Cl.
 CPC ........ *A61K 36/185* (2013.01); *A61K 2236/11* (2013.01); *A61K 2236/31* (2013.01)
(58) Field of Classification Search
 CPC .............. A61K 36/185; A61K 2236/11; A61K 2236/31
 See application file for complete search history.

(56) References Cited

U.S. PATENT DOCUMENTS

| 2016/0219892 A1 | 8/2016 | Romanek |
| 2018/0296616 A1 | 10/2018 | Rivas |

| 2019/0281871 A1 | 9/2019 | Peet et al. |
| 2019/0321330 A1 | 10/2019 | Geiling et al. |
| 2020/0281890 A1 | 9/2020 | MacNair et al. |

(Continued)

FOREIGN PATENT DOCUMENTS

| EP | 3771330 A1 | 2/2021 |
| FR | 3098683 A1 | 1/2021 |

(Continued)

OTHER PUBLICATIONS

Kanazawa, K., et al., "Short Photoirradiation Induces Flavonoid Synthesis and Increases Its Production in Postharvest Vegetables" Journal of Agricultural and Food Chemistry, vol. 60, No. 17 pp. 4359-4368 (2012), 10 pages.

Assumpção, C. F., et al., "Different Carotenoid Enrichment in Two Climacteric Fruits after Post-Harvest UV-B Treatment" Current Bioactive Compounds, vol. 16, No. 2, pp. 102-108, (2020), 7 pages.

(Continued)

*Primary Examiner* — Nicole M Ippolito
*Assistant Examiner* — Hanway Chang
(74) *Attorney, Agent, or Firm* — Hunton Andrews Kurth LLP

(57) ABSTRACT

Provided is a method of treating a post-harvest plant after harvest, the method including: irradiating a harvested plant with light having a peak wavelength in a wavelength range from 270 to 290 nm and/or light having a peak wavelength in a wavelength range from 370 to 400 nm at an irradiance effective to increase an amount of at least one rare cannabinoid compound and/or at least one terpene compound in the harvested plant, wherein an irradiance of light of all wavelengths in a wavelength range from 410 to 700 nm received by the harvested plant during the irradiation is less than 20% of the irradiance of the light having a peak wavelength in the wavelength range from 270 to 290 nm and/or less than 20% of the irradiance of the light having a peak wavelength in the wavelength range from 370 to 400 nm.

20 Claims, 6 Drawing Sheets

(56) References Cited

U.S. PATENT DOCUMENTS

| | | |
|---|---|---|
| 2020/0289459 A1 | 9/2020 | Geiling et al. |
| 2021/0000789 A1 | 1/2021 | Wagner et al. |
| 2021/0112726 A1 | 4/2021 | Wu et al. |
| 2021/0186780 A1 | 6/2021 | Davis |

FOREIGN PATENT DOCUMENTS

| | | |
|---|---|---|
| JP | H11-1106 A | 1/1999 |
| JP | 2018145345 A | 9/2018 |
| JP | 2018186802 A | 11/2018 |
| JP | 2020014451 A | 1/2020 |
| JP | 2021013315 A | 2/2021 |
| WO | 2020214859 A1 | 10/2020 |
| WO | 2021096813 A1 | 5/2021 |

OTHER PUBLICATIONS

Liu, L.H., et al., "Effects of UV-C, red light and sun light on the carotenoid content and physical qualities of tomatoes during postharvest storage" Food Chemistry, vol. 115, No. 2, pp. 495-500 (2009), 6 pages.

Santin, M., et al., "The outer influences the inner: Postharvest UV-B irradiation modulates peach flesh metabolome although shielded by the skin" Food Chemistry, vol. 338, 127782, (2021), 12 pages.

Dyshlyuk, L., et al., "The effect of postharvest ultraviolet irradiation on the content of antioxidant compounds and the activity of antioxidant enzymes in tomato" Heliyon, vol. 6, No. 1, e03288, (2020), 8 pages.

Bravo, S., et al., "Effects of postharvest UV-C treatment on carotenoids and phenolic compounds of vine-ripe tomatoes" International Journal of Food Science and Technology, vol. 48, No. 8, pp. 1744-1749 (2013), 6 pages.

METHOD AND APPARATUS FOR TREATING POST-HARVEST PLANT

CROSS-REFERENCE TO RELATED APPLICATION

This application claims priority to Japanese Patent Application No. 2021-051885, filed on Mar. 25, 2021, the disclosure of which is hereby incorporated by reference in its entirety.

The present disclosure relates to a method and apparatus for treating a post-harvest plant.

Cannabinoid compounds and terpene compounds contained in plants are used for medical purposes in many countries. Recent studies have focused on the pharmacological effects of rare cannabinoids other than major cannabinoids (THC and CBD). Additionally, techniques have been developed to increase the amount of useful substances synthesized in a plant by irradiating the plant with light. For example, Japanese Patent Publication No. 2018-145345 describes a method of increasing the amount of a secondary metabolic substance contained in a flower of a dicotyledonous plant after harvest by irradiating the plant after harvest with ultraviolet light and then irradiating with blue light or red light while drying.

SUMMARY

There is a need for technology to efficiently increase the amount of a rare cannabinoid compound and/or a terpene compound in plants.

The present disclosure provides a method of treating a post-harvest plant, the method including:
irradiating a harvested plant with light having a peak wavelength in a wavelength range from 270 to 290 nm at an irradiance effective to increase amount of at least one rare cannabinoid compound and/or at least one terpene compound in the harvested plant and/or with light having a peak wavelength in a wavelength range from 370 to 400 nm at an irradiance effective to increase amount of at least one rare cannabinoid compound and/or at least one terpene compound in the harvested plant,
wherein an irradiance of light of all wavelengths in a wavelength range from 410 to 700 nm received by the harvested plant during the irradiating is less than 20% of the irradiance of the light having a peak wavelength in the wavelength range from 270 to 290 nm and/or less than 20% of the irradiance of the light having a peak wavelength in the wavelength range from 370 to 400 nm.

The present disclosure also provides a method of manufacturing a product containing at least one rare cannabinoid compound and/or at least one terpene compound, the method including drying a product made by the treatment method described above.

The present disclosure also provides a method of manufacturing an extract containing a rare cannabinoid compound or terpene compound, the method including extracting at least one rare cannabinoid compound or at least one terpene compound from a product made by the treatment method described above.

The present disclosure also provides a method of manufacturing a rare cannabinoid compound or a terpene compound, the method including purifying a rare cannabinoid compound or a terpene compound from a product made by the treatment method described above.

The present disclosure also provides a plant treatment apparatus including:
a holding unit configured to hold a harvested plant; and
an irradiation unit configured to emit light having a peak wavelength in a wavelength range from 270 to 290 nm and light having a peak wavelength in a wavelength range from 370 to 400 nm,
wherein the irradiation unit is configured to emit the light having the peak wavelength in the wavelength range from 270 to 290 nm and/or the light having the peak wavelength in the wavelength range from 370 to 400 nm toward a harvested plant held by the holding unit to irradiate the harvested plant.

According to the present disclosure, the amount of a rare cannabinoid compound and/or a terpene compound in a plant can be efficiently increased.

DESCRIPTION OF EMBODIMENTS

Figure 1:
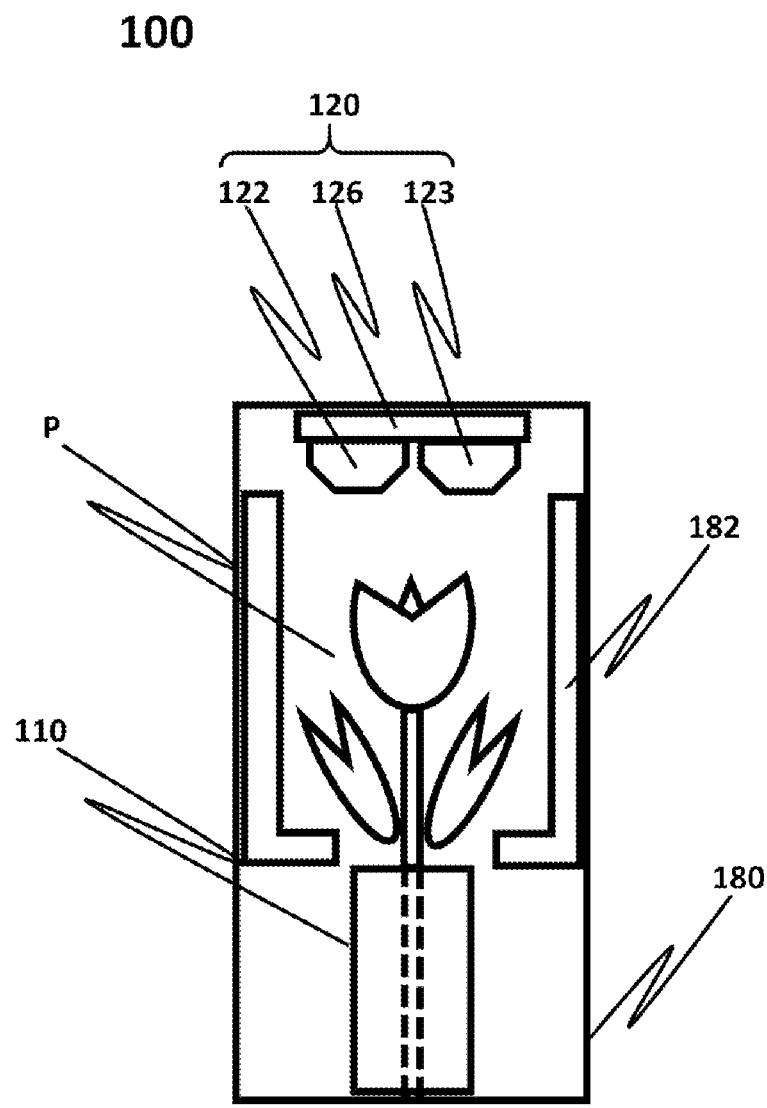
FIG. 1 is an exemplary schematic diagram illustrating an embodiment of an apparatus of the present disclosure.

The present disclosure provides, from one viewpoint, a method of treating a post-harvest plant, the method including irradiating a harvested plant with light having a peak wavelength in a wavelength range from 270 to 290 nm and/or light having a peak wavelength in a wavelength range from 370 to 400 nm at an irradiance effective to increase an amount of at least one rare cannabinoid compound and/or at least one terpene compound in the plant, in which an irradiance of light of all wavelengths in a wavelength range from 410 to 700 nm received by the harvested plant during the irradiation is less than 20% of the irradiance of the light having a peak wavelength in the wavelength range from 270 to 290 nm and/or less than 20% of the irradiance of the light having a peak wavelength in the wavelength range from 370 to 400 nm.

In the present disclosure, a numerical range "from a to b" (where "a" and "b" are specific numerical values) means a range including both end values "a" and "b". In other words, "from a to b" is synonymous with "a or greater and b or less", "a or higher and b or lower", or "a or more and b or less" unless it is clear that this is not the case.

In the present disclosure, the "harvested plant", the "plant after harvest", or the "post-harvest plant" (both terms are used interchangeably in the present specification) refers to a plant which lacks nutritional supply and water supply through the root and can biosynthesize a cannabinoid compound and/or a terpene compound (synthesis by the action of the plant enzyme). In this case, the water supply refers to another source of water supply other than the water vapor contained in the surrounding atmosphere. Alternatively, the "harvested plant", the "plant after harvest", or the "post-harvest plant" refers to a plant which is not receiving photosynthetically active radiation (PAR) at a photosynthetic photon flux density (PPFD) higher than the light compensation point of the plant and can biosynthesize a cannabinoid compound and/or a terpene compound.

To avoid complications, the term simply referred to as "plant" in the present disclosure refers to a plant after harvest unless it is clear from the context that such a limitation should not be applied.

The post-harvest plant is not limited in terms of the cultivation method before harvest. Thus, the post-harvest plant may be a plant that has been grown in soil (e.g., grown outdoors or grown in greenhouse) before harvest or grown in a nutrient solution (e.g., hydroponics, solid medium cultivation, or spray cultivation) before harvest. When the treatment method of the present disclosure is implemented for the purpose of manufacturing pharmaceuticals or food products, the post-harvest plant is preferably a plant that has been grown in nutrient solution (especially under aseptic conditions) before harvest. In addition, the post-harvest plant may also be a plant grown from a seed or a clonal plant (e.g., by cutting propagation or callus culture).

A duration of the time from harvest to the irradiation is not particularly limited as long as the post-harvest plant can biosynthesize at least one rare cannabinoid compound and/or at least one terpene compound, but can be, for example, within 2 weeks, more specifically within 10 days, more specifically within 1 week, more specifically within 5 days, more specifically 2 days, more specifically within 24 hours, more specifically within 12 hours, more specifically within 6 hours, more specifically within 3 hours, more specifically within 2 hours, and more specifically within 1 hour.

The post-harvest plant is preferably a plant freshly preserved at the time of the irradiation. In the present disclosure, "freshness" means the ability of the post-harvest plant to biosynthesize at least one rare cannabinoid compound and/or at least one terpene compound, and "freshly preserved" means preserving freshness at the time of the irradiation.

Treatment for preserving freshness can, for example, be storing the post-harvest plant in a dark place, and/or supplying the post-harvest plant with a liquid including water, and/or storing the post-harvest plant at low temperature.

In the present disclosure, the "dark place" refers to a space where the PPFD is not higher than the light compensation point of the plant or 10 μmol/m²/s or lower (more specifically 5 μmol/m²/s or lower, more specifically 2 μmol/m²/s or lower, and more specifically 1 μmol/m²/s or lower).

In the present disclosure, "storing at low temperature" or "low-temperature storage" refers to storing in an environment in a range from 0 to 15° C., for example, in a range from 0 to 10° C., more specifically in a range from 1 to 10° C., more specifically in a range from 4 to 10° C., and more specifically in a range from 4 to 8° C.

The liquid containing water can be supplied to the plant, for example, by spraying, immersion, or contact with a water-holding material (e.g., a water-absorbing polymer). When the plant is harvested by cutting (e.g., cutting the stem), the liquid is preferably supplied from the cut surface.

When the liquid is supplied by spraying, the spraying may be a continuous spraying or intermittent spraying. In the present disclosure, the "liquid containing water" can be water (including tap water); or water containing at least one substance selected from the group consisting of precursor substances of rare cannabinoid compounds and/or terpene compounds, and plant hormones. Examples of the precursor substance include amino acids, such as phenylalanine and tyrosine; and metabolites of the glycolysis, such as pyruvic acid and acetyl-CoA. Examples of the plant hormone include hormones promoting biosynthesis, such as abscisic acid. An additive may be added to the liquid containing water. Examples of such an additive include: an alcohol for the purpose of sterilization; a surfactant for improving water uptake; an acid, such as vinegar or citric acid, for an antibacterial/bacteriostatic action; a sugar as an energy source; or a plant senescence hormone, such as a vitamin or an inorganic salt, for preventing plant senescence. However, when the treatment method of the present disclosure is implemented for the purpose of manufacturing pharmaceuticals or food products, the liquid containing water preferably contains no additive. The water contained in the liquid is preferably sterile water.

The treatment for preserving the freshness is preferably started as early as possible after harvest; the treatment can be started, for example, within 6 hours after harvest, more specifically within 4 hours, more specifically within 2 hours, more specifically within 1 hour, more specifically within 30 minutes, and is most preferably started immediately after harvest. The treatment for preserving the freshness is preferably continued until immediately before the irradiation.

In the present disclosure, the post-harvest plant to be irradiated with ultraviolet light in the irradiation (hereinafter also referred to simply as the "plant to be irradiated") may be in the form of a whole plant including a shoot system and a root system or may be in the form of a part of a plant, such as a root or a shoot. The shoot includes at least one of a stem, leaf, flower, or fruit (which may be a part of each and can be, for example, a pericarp). The plant to be irradiated can, for example, be a shoot system including a flower, leaf, and pericarp, or a shoot system including a flower and/or leaf and/or stem (more specifically, a shoot system composed of a flower and stem and optionally a leaf, or a shoot system composed of a stem and leaf). The stem includes a rachis, peduncle, and flower stalk. The flower can be a spike. In the present disclosure, a part of the plant includes a seed and, if applicable, a trichome.

In the present disclosure, the seed of the plant to be irradiated is any seed of a plant that can produce at least one rare cannabinoid compound and/or at least one terpene compound and not particularly limited. The seed of the plant to be irradiated can, for example, be one having a UVR8 photoreceptor.

Specific examples of the plant to be irradiated include, but are not limited to, the family Cannabaceae (e.g., plants of the genus *Cannabis* (e.g., *Cannabis sativa*) and plants of the genus *Humulus* (e.g., hops (*Humulus lupulus*)), plants of the family Apiaceae (e.g., plants of the genus *Carum* (e.g., caraway (*Carum carvi*)), plants of the genus *Foeniculum* (e.g., fennel (*Foeniculum vulgare*)), plants of the genus *Anethum* (e.g., dill (*Anethum graveolens*)), plants of the genus *Angelica* (e.g., *Angelica archangelica*), plants of the genus *Petroselinum* (e.g., parsley (*Petroselinum crispum*)), and plants of the genus *Coriandrum* (e.g., coriander (*Coriandrum sativum* L.)), plants of the family Asteraceae (e.g., plants of the genus *Artemisia* (e.g., tarragon (*Artemisia dracunculus*) and *Artemisia vulgaris*), plants of the family Rosaceae (e.g., plants of the genus *Rosa* (e.g., roses) and plants of the genus *Matricaria* (e.g., chamomile (*Matricaria recutita*)), plants of the family Piperaceae (e.g., plants of the genus *Piper* (e.g., pepper (*Piper nigrum*)), plants of the family Lamiaceae (e.g., plants of the genus *Mentha*, plants of the genus *Ocimum* (e.g., basil (*Ocimum basilicum*)), plants of the genus *Lavandula*, and plants of the genus *Salvia* (e.g., clary sage (*Salvia sclarea*)), plants of the family Verbenaceae (e.g., plants of the genus *Verbena* (e.g., *verbena*)), plants of the family Poaceae (e.g., plants of the genus *Cymbopogon* (e.g., lemongrass (*Cymbopogon citratus*)), plants of the family Orchidaceae, plants of the family Amaryllidaceae (e.g., *Narcissus tazetta* var. *chinensis*), plants of the family Zygophyllaceae (e.g., plants of the genus *Guaiacum* (e.g., guaiacum (*Guaiacum officinale*)), plants of the family Lauraceae (e.g., plants of the genus *Laurus* (e.g., laurel (*Laurus nobilis*), plants of the genus *Aniba* (e.g., rosewood (*Aniba rosaeodora*)), plants of the genus *Cinnamomum* (e.g., *Cinnamomum camphora* ssp.), and plants of the genus *Lindera* (e.g., *Lindera aggregata*)), plants of the family Myrtaceae of the order Myrtales (e.g., plants of the genus *Eucalyptus*), plants of the family Rutaceae (e.g., plants of the genus *Fortunella* and plants of the genus *Citrus* (e.g., bitter orange (*Citrus aurantium*), bergamot (*Citrus* x *bergamia*), grapefruit (*Citrus* x *paradisi*), mandarin orange (*Citrus reticulata*), lemon (*Citrus limon*), and orange (*Citrus sinensis*)), plants of the family Burseraceae (e.g., plants of the genus *Brucella* (e.g., linaloe (*Bursera delpechiana*)) and plants of the genus *Boswellia*), and plants of the family Cupressaceae (e.g., cypress pine (*Callitris columellaris* F. Muell.).

The plant to be irradiated may be genetically engineered; for example, an enzyme involved in the synthesis system of a rare cannabinoid compound and/or a terpene compound or a gene for a photoreceptor, such as UVR-8, which has sensitivity to the UVA region or the UVB region, may be engineered.

In a certain embodiment, the plant to be irradiated is a plant of the genus *Cannabis*. In the present disclosure, the plant of the genus *Cannabis* is any plant belonging to the genus *Cannabis* of the family Cannabaceae and not particularly limited and includes any species (also referred to as a "strain" in the present disclosure) (progenitors, varieties, and cultivars/horticultural varieties) of *Cannabis sativa* Linnaeus, *Cannabis indica* Lamarck or *C. sativa* subsp. *indica*, *Cannabis ruderalis* Janischewsky or *C. sativa* subsp. *ruderalis*, *C. sativa* subsp. *sativa* var. *spontanea* (or *C. sativa* subsp. *spontanea*), and *C. sativa* subsp. *indica* var. *kafiristanica* (or *C. sativa* subsp. *kafiristanica*), and their genetically engineered versions. The cultivars/horticulture varieties include hybrids (in particular, a hybrid of *C. sativa* and *C. indica*).

The plants of the genus *Cannabis* can be classified into high THC strains, high CBD strains, and THC-CBD balanced strains according to the content percentage of tetrahydrocannabinol (THC) and cannabidiol (CBD). In the present disclosure, the high THC strain refers to a strain with a content of THC in a flower after drying (e.g., natural drying or air drying for about two weeks) of 10% or higher. Similarly, the high CBD strain is a strain with a CBD content of 10% or higher, and the THC-CBD balanced strain is a strain with contents of both THC and CBD of less than 10%.

Specific examples of the high THC strain include BLK Label, Barak, Erez, Jasmin, Tal, Shira, Or, El-na, Alaska, Eran-Almog, Dorit, Omer, Zohar, Afina, Ludina, and Talea. Specific examples of the high CBD strain include MUN shine 6, Avidekel, and Rafael. Specific examples of the THC-CBD balanced strain include RGM Argvana Heart, Mango, and Elida.

In an exemplary treatment method of the present disclosure, the harvested plant may be irradiated with light having a peak wavelength in a wavelength range from 270 to 290 nm, more specifically a wavelength range from 273 to 287 nm, more specifically a wavelength range from 275 to 285 nm, and/or light having a peak wavelength in a wavelength range from 370 to 400 nm, more specifically a wavelength range from 375 to 395 nm, and more specifically a wavelength range from 380 to 390 nm.

Hereinafter, the description of the light having a peak wavelength in the wavelength range from 270 to 290 nm also applies to the light having a peak wavelength in the wavelength range from 273 to 287 nm and the light having a peak wavelength in the wavelength range from 275 to 285 nm, and the description of the light having a peak wavelength in the wavelength range from 370 to 400 nm also applies to the light having a peak wavelength in the wavelength range from 375 to 395 nm and the light having a peak wavelength in the wavelength range from 380 to 390 nm.

The light having a peak wavelength in the wavelength range from 270 to 290 nm and the light having a peak wavelength in the wavelength range from 370 to 400 nm can each increase the amount of at least one rare cannabinoid compound and/or at least one terpene compound in the irradiated post-harvest plant.

In some embodiments, the post-harvest plant is irradiated with the light having a peak wavelength in the wavelength range from 270 to 290 nm.

In some other embodiments, the post-harvest plant is irradiated with the light having a peak wavelength in the wavelength range from 370 to 400 nm.

In yet some other embodiments, the post-harvest plant is irradiated with the light having a peak wavelength in the wavelength range from 270 to 290 nm and the light having a peak wavelength in the wavelength range from 370 to 400 nm. Irradiation with the two types of light can effectively increase a rare cannabinoid compound and/or a terpene compound in the plant to be irradiated. The two types of light can be emitted sequentially or simultaneously to irradiate the plant. In a more specific embodiment, the harvested plant is first irradiated with the light having a peak wavelength in the wavelength range from 270 to 290 nm and then irradiated with the light having a peak wavelength in the wavelength range from 370 to 400 nm; alternatively, the harvested plant is irradiated with the light having a peak wavelength in the wavelength range from 370 to 400 nm and then irradiated with the light having a peak wavelength in the wavelength range from 270 to 290 nm. In this embodiment, an interval between the irradiation with the light having a peak wavelength in the wavelength range from 270 to 290 nm and the irradiation with the light having a peak wavelength in the wavelength range from 370 to 400 nm is not particularly limited but can be, for example, in a range from 30 seconds to 2 hours, more specifically from 30 seconds to 1 hour, more specifically from 30 seconds to 30 minutes, more specifically from 30 seconds to 15 minutes, more specifically from 30 seconds to 10 minutes, and more specifically from 30 seconds to 5 minutes.

In another more specific embodiment, the post-harvest plant is irradiated simultaneously with the light having a peak wavelength in the wavelength range from 270 to 290 nm and the light having a peak wavelength in the wavelength range from 370 to 400 nm. A duration of the simultaneous irradiation is not particularly limited, but for example, the post-harvest plant can be irradiated with the light having a peak wavelength in the wavelength range from 370 to 400 nm for a duration of 40% or greater, more specifically a duration of 50% or greater, more specifically a duration of 70% or greater, more specifically a duration of 90% or greater, or more specifically a duration of 95% or greater of a duration of the irradiation with the light having a peak wavelength in the wavelength range from 270 to 290 nm.

The irradiance of the light having a peak wavelength in the wavelength range from 270 to 290 nm and/or the light having a peak wavelength in the wavelength range from 370 to 400 nm is any amount effective to increase the amount of at least one rare cannabinoid compound and/or at least one terpene compound in the post-harvest plant irradiated and not particularly limited.

For the light having a peak wavelength in the wavelength range from 270 to 290 nm, the amount effective to increase the amount of at least one rare cannabinoid compound and/or at least one terpene compound can be, for example, in a range from 2250 to 54000 $\mu mol/m^2$, more specifically in a range from 3000 to 45000 $\mu mol/m^2$, more specifically in a range from 4500 to 36000 $\mu mol/m^2$, more specifically in a range from 6000 to 27000 $\mu mol/m^2$, and more specifically in a range from 7500 to 22500 $\mu mol/m^2$.

For the light having a peak wavelength in the range from 370 to 400 nm, the amount effective to increase the amount of at least one rare cannabinoid compound and/or at least one terpene compound can be, for example, in a range from 33750 to 1620000 $\mu mol/m^2$, more specifically in a range from 50000 to 1450000 $\mu mol/m^2$, more specifically in a range from 80000 to 1200000 $\mu mol/m^2$, more specifically in a range from 100000 to 1000000 $\mu mol/m^2$, and more specifically in a range from 120000 to 750000 $\mu mol/m^2$.

When the plant to be irradiated is a high THC strain or a THC-CBD balanced strain of plants of the genus *Cannabis*, the irradiance of the irradiation light having a peak wavelength in the wavelength range from 270 to 290 nm is, for example, in a range from 9000 to 27000 $\mu mol/m^2$, and more specifically can be in a range from 10000 to 25000 $\mu mol/m^2$, more specifically in a range from 12000 to 22000 $\mu mol/m^2$, and more specifically in a range from 15000 to 20000 $\mu mol/m^2$.

When the plant to be irradiated is a high THC strain of plants of the genus *Cannabis*, the irradiance of the irradiation light having a peak wavelength in the wavelength range from 370 to 400 nm can be, for example, in a range from 270000 to 810000 $\mu mol/m^2$, more specifically in a range from 400000 to 700000 $\mu mol/m^2$, more specifically in a range from 450000 to 650000 $\mu mol/m^2$, and more specifically in a range from 500000 to 600000 $mol/m^2$.

When the plant to be irradiated is a high CBD strain of plants of the genus *Cannabis*, the irradiance of the irradiation light having a peak wavelength in the wavelength range from 370 to 400 nm can be, for example, in a range from 67000 to 210000 $\mu mol/m^2$, more specifically in a range from 75000 to 180000 $\mu mol/m^2$, more specifically in a range from 90000 to 165000 $\mu mol/m^2$, and more specifically in a range from 100000 to 150000 $\mu mol/m^2$.

The photon flux density of the light having a peak wavelength in the wavelength range from 270 to 290 nm and/or the light having a peak wavelength in the wavelength range from 370 to 400 nm is not particularly limited as long as the irradiance is employed in an amount in combination with the irradiation time effective to increase the amount of at least one rare cannabinoid compound and/or at least one terpene compound in the irradiated post-harvest plant. From the viewpoint of efficiency, the lower limit of the photon flux density for the light having a peak wavelength in the wavelength range from 270 to 290 nm can be, for example, 0.1 $\mu mol/m^2/s$ or greater, and more specifically can be 0.5 $\mu mol/m^2/s$, 1 $\mu mol/m^2/s$, or 2 $\mu mol/m^2/s$. For the light having a peak wavelength in the wavelength range from 370 to 400 nm, the lower limit of the photon flux density can be, for example, 5 $\mu mol/m^2/s$ or greater, and more specifically can be 10 $\mu mol/m^2/s$, 20 $\mu mol/m^2/s$, 50 $\mu mol/m^2/s$, or 100 $\mu mol/m^2/s$. From the viewpoint of plant damage, the upper limit of the photon flux density for the light having a peak wavelength in the wavelength range from 270 to 290 nm can be, for example, 100 $\mu mol/m^2/s$ or less, and more specifically can be 50 $\mu mol/m^2/s$ or less, 20 $\mu mol/m^2/s$, or 10 $\mu mol/m^2/s$. For the light having a peak wavelength in the wavelength range from 370 to 400 nm, the upper limit of the photon flux density can be, for example, 2000 $\mu mol/m^2/s$ or less, and more specifically can be 1000 $\mu mol/m^2/s$, 750 $\mu mol/m^2/s$, 500 $\mu mol/m^2/s$, or 300 $\mu mol/m^2/s$.

The irradiation time of the light having a peak wavelength in the wavelength range from 270 to 290 nm and/or the light having a peak wavelength in the wavelength range from 370 to 400 nm is not particularly limited as long as the irradiance is employed in an amount in combination with the photon flux density effective to increase the amount of at least one rare cannabinoid compound and/or at least one terpene compound in the irradiated post-harvest plant. From the viewpoint of efficiency, the irradiation time can be, for example, in a range from 30 seconds to 24 hours, more specifically in a range from 1 minute to 12 hours, more specifically in a range from 2 minutes to 6 hours, more specifically in a range from 5 minutes to 4 hours, more specifically in a range from 10 minutes to 2 hours, and more specifically in a range from 15 minutes to 1 hour.

Light in a wavelength range from 410 to 700 nm is less effective in or does not contribute to increasing the amount of the rare cannabinoid compound and/or the terpene compared with the light having a peak wavelength in the wavelength range from 270 to 290 nm and/or the light having a peak wavelength in the wavelength range from 370 to 400 nm. Thus, from the viewpoint of efficiency, an irradiance of the light of all wavelengths in the wavelength range from 410 to 700 nm received by the plant to be irradiated during the irradiation is preferably less than 20% of the irradiance of the light having a peak wavelength in the wavelength range from 270 to 290 nm and/or less than 20% of the irradiance of the light having a peak wavelength in the wavelength range from 370 to 400 nm, more preferably less than 10%, more preferably less than 5%, more preferably less than 2%, and more preferably less than 1%. In addition, the irradiation may be performed in a dark place or under indoor lighting. In performing the irradiation under indoor lighting, the irradiance of the light of all wavelengths in the wavelength range from 410 to 700 nm received by the plant to be irradiated during the irradiation including the irradiance of the light of the indoor lighting is preferably adjusted to less than 20% of the irradiance of the light having a peak wavelength in the wavelength range from 270 to 290 nm and/or less than 20% of the irradiance of the light having a peak wavelength in the wavelength range from 370 to 400 nm.

From another viewpoint, the illuminance (PPFD) of the light in the wavelength range from 400 to 700 nm received by the plant to be irradiated during the irradiation can be not higher than the light compensation point of the plant. The irradiation with a PPFD not higher than the light compensation point can suppress the activation of the pathway that does not contribute to the synthesis of the rare cannabinoid compound and/or the terpene compound and thus can efficiently increase the rare cannabinoid compound and/or the terpene compound.

On the other hand, the maximum absorption wavelength of DNA and RNA is at or near 260 nm, and thus this leads to a concern that light with a wavelength of 260 nm or lower has a great negative effect on plants, for example, cell damage. Thus, the irradiance of light of all wavelengths in a wavelength range from 200 to 260 nm received by the plant to be irradiated during the irradiation is preferably less than 20% of the irradiance of the light having a peak wavelength in the wavelength range from 270 to 290 nm and/or the light having a peak wavelength in the wavelength range from 370 to 400 nm, more preferably less than 10%, more preferably less than 5%, more preferably less than 2%, and more preferably less than 1%.

Light sources to be used to irradiate the plant to be irradiated with the light having a peak wavelength in the wavelength range from 270 to 290 nm and/or the light having a peak wavelength in the wavelength range from 370 to 400 nm is any light source which can emit each specified light and not particularly limited, and, for example, a commonly used ultraviolet light source, such as a UV lamp, can be used. For the UV lamp, for example, a xenon lamp, a metal halide lamp, or a high-pressure mercury lamp is preferably used. In addition, light filtered from sunlight by an optical filter or the like may be used.

When the light source to be used is a light source emitting the light in the wavelength range from 410 to 700 nm with an amount of radiation 20% or more of the amount of radiation of the light having a peak wavelength in the wavelength range from 270 to 290 nm and/or the light having a peak wavelength in the wavelength range from 370 to 400 nm, a filter with a higher transmittance for the latter light than that for the former light can be used in conjunction with the light source. Similarly, when the light source to be used is a light source emitting the light in the wavelength range from 200 to 260 nm with an amount of radiation 20% or more of the amount of radiation of the light having a peak wavelength in the wavelength range from 270 to 290 nm and/or the light having a peak wavelength in the wavelength range from 370 to 400 nm, a filter with a higher transmittance for the latter light than that for the former light can be used in conjunction with the light source.

From the viewpoint of energy efficiency, the light having a peak wavelength in the wavelength range from 270 to 290 nm can have a full width at half maximum (FWHM), for example, in a range from 0.1 to 20 nm, more specifically in a range from 0.1 to 15 nm, more specifically in a range from 0.1 to 10 nm, and more specifically in a range from 0.1 to 5 nm. In a certain embodiment, the light having a peak wavelength in the wavelength range from 270 to 290 nm and the light having a peak wavelength in the wavelength range from 370 to 400 nm are light having a single peak in each wavelength range. In a specific example, the light having a peak wavelength in the wavelength range from 270 to 290 nm is light having a spectrum with a peak wavelength of 280±5 nm and a full width at half maximum in a range from 0.1 to 10 nm, and the light having a peak wavelength in the wavelength range from 370 to 400 nm is light having a spectrum with a peak wavelength of 385±5 nm and a full width at half maximum in a range from 0.1 to 10 nm.

The light source to be used to emit the light having a peak wavelength in the wavelength range from 270 to 290 nm and/or the light having a peak wavelength in the wavelength range from 370 to 400 nm is preferably a light emitting diode (LED) or a laser diode (LD) having a single peak in the light emission spectrum. The method using an LED or LD as a light source can easily achieve irradiation with the light in a wavelength range effective to increase the amount of the rare cannabinoid compound and/or the terpene compound in the post-harvest plant while avoiding irradiation with light in a wavelength that does not contribute or contributes a little to increasing the amount and/or light in a wavelength that can be harmful to the plant. In addition, the use of an LED or LD is preferred also from the viewpoints of energy efficiency and economy due to energy aggregation, low heat generation, low power consumption, and long life. Additionally, the use of an LED or LD facilitates control/management of the irradiance.

The light having a peak wavelength in the wavelength range from 270 to 290 nm and/or the light having a peak wavelength in the wavelength range from 370 to 400 nm can each be emitted as continuous light or as intermittent light, such as pulsed light, or as their combination but is preferably intermittent light. The use of intermittent light can avoid or reduce the temperature rise of the plant to be irradiated and/or a light source. Specific examples of the intermittent light include those with a pulse width of 100 ms or less, more specifically 50 ms or less, more specifically 20 ms or less, more specifically 10 ms or less, and more specifically 5 ms or less, and a duty ratio of 50% or less, more specifically 40% or less, more specifically 30% or less, more specifically 20% or less, more specifically 10% or less, and more specifically 5% or less.

In the present disclosure, the rare cannabinoid compound refers to a cannabinoid compound other than tetrahydrocannabinol (Δ9-THC) and tetrahydrocannabinolic acid (Δ9-THCA), and cannabidiol (CBD) and cannabidiolic acid (CBDA) (in the present disclosure, the above four compounds may be collectively referred to as the "major cannabinoid compounds") among those that can be naturally synthesized in the plant to be used. The cannabinoid compound that can be naturally synthesized in the plant includes a cannabigerol type (e.g., cannabigerol-C5 (CBG-C5), cannabigerol-C5 monomethyl ether (CBGM-C5), cannabigerolic acid-C5 (CBGA-C5), cannabigerovarin (CBGV-C3), cannabigerolic acid-C5 monomethyl ether (CBGAM-C5), cannabigerovaric acid (CBGVA-C3), cannabigerol-C6 (CBG-C6), cannabigerolic acid-C6 (CBG-C6), cannabigerol-C4 (CBG-C4), cannabigerolic acid-C4 (CBG-C4), and sesquicannabigerol (sesqui-CBG)), a cannabidiol type (e.g., cannabidiol-C5 (CBD-C5), cannabidiol monomethyl ether (CBDM-C5), cannabidiol-C4 (CBD-C4), cannabidivarin (CBDV-C3), cannabidiolic acid (CBDA-C5), cannabidivarinic acid (CBDVA-C3), cannabidiol-C7 (CBD-C7), cannabidiolic acid-C7 (CBDA-C7), and cannabidiolic acid-C4 (CBD-C4)), a cannabinodiol type (e.g., cannabinodiol (CBND-C5), cannabinodivarin (CBND-C3), cannabinodiolic acid (CBND-C5), and cannabinodivarinic acid (CBND-C3)), a cannabinol type (e.g., cannabinol-C5 (CBN-C5), cannabinol-C4 (CBN-C4), cannabinol-C2 (CBN-C2), cannabivarin (CBN-C3), cannabinolic acid (CBNA-C5), and cannabinol methyl ether (CBNM-C5)), a cannabichromene type (e.g., cannabichromene (CBC-C5), cannabichromenic acid (CBCA-C5), cannabivarichromene, cannabichromevarin (CBCV-C3), and cannabichromevarinic acid (CBCVA-C3)), a cannabicyclol type (e.g., cannabicyclol (CBL-C5), cannabicyclolic acid (CBLA-C5), and cannabicyclovarin (CBLV-C3)), a cannabielsoin type (e.g., cannabielsoin-C5 (CBE-C5), cannabielsoin-C3 (CBE-C3), cannabielsoinic acid-C5 (CBEA-C5), and cannabielsoinic acid-C3 (CBEA-C3)), a cannabitriol type (e.g., cannabitriol- C5 (CBT-C5), cannabitriol-C3 (CBT-C3), cannabitriol-1 (CBT-1), cannabitriolic acid-C5 (CBTA-C5), and cannabitiolic acid-C3 (CBTA-C3)), a tetrahydrocannabinol type (e.g., Δ9-tetrahydrocannabinol-C5 (Δ9-THC-C5), Δ9-tetrahydrocannabinol-C4 (Δ9-THC-C4), Δ9-tetrahydrocannabivarin-C3 (Δ9-THCV-C3), Δ9-tetrahydrocannabinolic acid-C5 (Δ9-THCA-C5), Δ9-tetrahydrocannabinolic acid-C4 (Δ9-THCA-C4), and Δ9-tetrahydrocannabivarinic acid-C3 (Δ9-THCVA-C3)), and an iso-tetrahydrocannabinol type (e.g., Δ7-isotetrahydrocannabinol and Δ7-isotetrahydrocannabivarin), and a cannabicitran type (e.g., cannabicitran (CBT-C5)).

In a specific example, the rare cannabinoid compound is one or more compound selected from the group consisting of tetrahydrocannabinol-C4 (THC-C4), cannabitriol-3 (CBT-3), cannabinodiolic acid (CBNDA), cannabitriolic acid-3 (CBTA-3), cannabitriolic acid-1 (CBTA-1), cannabidiol-4 (CBD-4), cannabielsovarinic acid (CBEVA), cannabitriol-1 (CBT-1), cannabivarinic acid (CBNVA), cannabigerol-C6 (CBG-C6), cannabigerolic acid-C4 (CBGA-C4), sesquicannabigerol (Sesqui-CBG), cannabidiolic acid-C7 (CBDA-C7), cannabichromevarinic acid (CBCVA), cannabigerolic acid-C6 (CBGA-C6), and cannabielsoinic acid (CBEA).

In the present disclosure, the terpene compound refers to a terpene compound that can be naturally synthesized in the plant to be used and includes terpenoids. The terpene compound that can be naturally synthesized in the plant includes monoterpene compounds, sesquiterpene compounds, and diterpene compounds. The terpene compound shares a precursor substance with the cannabinoid compound in the plant.

Examples of the monoterpene compound include: acyclic monoterpene compounds, such as ocimene, β-myrcene, geraniol, citral, citronellal, citronellol, β-citronellol, linalool, nerol, myrcenol, dihydromyrcenol, and lavandulol; monocyclic monoterpene compounds, such as limonene, terpinene, phellandrene, terpinolene, cymene, menthol, thymol, carvacrol, α-terpineol, menthane, 1,8-cineole (eucalyptol), pulegone, bisabolene, and carveol; and polycyclic monoterpene compounds, such as α-pinene, β-pinene, carene, sabinene, camphene, thujene, borneol, cineole, fenchol, camphor, and bergamotene. Examples of the sesquiterpene compound include: monocyclic sesquiterpene compounds, such as guaiol, α-bisabolol, β-bisabolol, α-humulene, curcumene, elemene, and bisabolene; acyclic sesquiterpene compounds, such as α-farnesene, β-farnesene, and nerolidol; and polycyclic sesquiterpene compounds, such as β-caryophyllene, caryophyllene oxide, valencene, β-eudesmol, ledene, selinene, cadinene, copaene, and guaiene. Examples of the diterpene compound include: phytol and geranylgeraniol.

In a specific example, the terpene compound is one or more compound selected from the group consisting of β-myrcene, ocimene, linalool, limonene, nerol, terpinolene, α-pinene, β-pinene, α-terpineol, borneol, fenchol, guaiol, α-bisabolol, α-humulene, β-farnesene, β-caryophyllene, caryophyllene oxide, nerolidol, valencene, phytol, geraniol, camphor, β-eudesmol, and ledene.

In the present disclosure, "to increase the amount of at least one rare cannabinoid compound and/or at least one terpene compound" or an "increased content of at least one rare cannabinoid compound and/or at least one terpene compound" refers to an increase in the amount of at least one rare cannabinoid compound and/or at least one terpene compound compared with that in a post-harvest plant not irradiated with light by the treatment method of the present disclosure, and refers to an increase, for example, to 110% or greater, more preferably to 120% or greater, more preferably to 130% or greater, more preferably to 140% or greater, more preferably to 150% or greater, more preferably to 160% or greater, more preferably to 170% or greater, more preferably to 180% or greater, more preferably to 190% or greater, and more preferably to 200% or greater when the amount of the rare cannabinoid compound and/or the terpene compound in the non-irradiated post-harvest plant is 100%.

Quantification of the rare cannabinoid compound and/or the terpene compound may be performed using any of known methods, can be performed, for example, by chromatography or mass spectrometry (MS), or any combination of them, and can also be performed in combination with electrospray ionization (ESI), flame ionization detection (FID), and/or supercritical fluid extraction (SFE). The chromatography can be, for example, gas chromatography (GC), liquid chromatography (LC) (e.g., high performance liquid chromatography (HPLC), ultra-high performance high separation liquid chromatography (UPLC), high performance thin-layer chromatography (HPTLC)), or supercritical fluid chromatography (SFC). Specific examples of the measurement method include GC-FID, GC/MS, LC/MS, MS/MS, GC/MS/MS, LC/MS/MS, ESI-MS/MS, ESI-LC/MS, ESI-LC/MS/MS, SFE-MS, SFE-MS/MS, SFE-SFC/MS, SFE-LC, and SFE-LC/MS. The rare cannabinoid compound and the terpene compound may be quantified by different methods. For example, the rare cannabinoid compound may be measured by LC/MS, and the terpene compound may be measured by GC/MS.

In some embodiments, a liquid containing water is supplied to the plant to be irradiated in the irradiation. The liquid containing water is as described above for the "treatment for preserving the freshness". The liquid can be supplied by any method that does not interfere with the light irradiation of the plant to be irradiated in the irradiation, and the method may be a continuous supply, for example, by spraying, immersion, or contact with a water-holding material, or may be intermittent supply, for example, by spraying.

The supply in the irradiation can suppress a loss in the freshness of the plant to be irradiated and can promote the synthesis of at least one rare cannabinoid compound and/or at least one terpene compound in the plant by the irradiation.

In some embodiments, the treatment method of the present disclosure further includes storing the plant in a dark place for 12 hours or longer immediately after the irradiation. The storage is preferably started as early as possible after the irradiation; the storage can be started, for example, within 1 hour after the irradiation, more specifically within 30 minutes, more specifically within 15 minutes, and is most preferably started immediately after the irradiation. Storing the plant in a dark place for 12 hours or longer after the irradiation allows the synthesis of at least one rare cannabinoid compound and/or at least one terpene compound by the irradiation to continue also during the storage, and thus this can further increase the amount of at least one rare cannabinoid compound and/or at least one terpene compound in the plant.

The storage can be more specifically 16 hours or longer, more specifically 20 hours or longer, more specifically 24 hours or longer, more specifically 28 hours or longer, more specifically 32 hours or longer, more specifically 36 hours or longer, more specifically 40 hours or longer, more specifically 44 hours or longer, and more specifically 48 hours or longer. The upper limit of the dark place storage time is not particularly limited as long as the content of at least one rare cannabinoid compound and/or at least one terpene compound in the plant is increased relative to the non-irradiated plant, but the upper limit can be, for example, 500 hours or shorter, more specifically 480 hours or shorter, more specifically 360 hours or shorter, more specifically 336 hours or shorter, more specifically 240 hours or shorter, more specifically 168 hours or shorter, and more specifically 120 hours or shorter.

The storage can be ambient temperature storage (storage at a temperature in a range from 15° C. to 30° C. although depending on the location and season) or low-temperature storage. In addition, during the storage, the plant may be supplied with the liquid containing water. In the storage, storing the plant in low temperature and/or supplying the plant with the liquid containing water can suppress loss in the freshness of the plant and thus can promote the synthesis of at least one rare cannabinoid compound and/or at least one terpene compound in the plant by the irradiation.

The dark place can be, for example, the inside of a storage or storage container, such as a refrigerator, the inside of a shipping container, or a luggage compartment of a freight car, aircraft, ship, or freight vehicle; or the inside of a light-shielding packaging material or packing material, such as a corrugated cardboard box.

The plant treated by the method described above contains an increased amount of at least one rare cannabinoid compound and/or at least one terpene compound than a non-treated plant and thus is suitable as a raw material for producing a product containing a rare cannabinoid compound and/or a terpene compound.

From another viewpoint, the present disclosure provides a method of manufacturing a product containing at least one plant rare cannabinoid compound and/or at least one terpene compound, the method including drying a plant treated by the method of treating a post-harvest plant described above.

In the present disclosure, the plant rare cannabinoid compound and/or the terpene compound means that the rare cannabinoid compound and/or the terpene compound is derived from a plant, and more specifically, is biosynthesized in the treated plant.

The drying can be performed by any of known methods. For example, the temperature in the drying can be, for example, a temperature in a range from 15 to 35° C., more specifically a temperature in a range from 18 to 30° C., and more specifically in a range from 20 to 27° C., and the relative humidity can be, for example, in a range from 20 to 70%, more specifically in a range from 25 to 65%, more specifically in a range from 30 to 60%, and more specifically in a range from 35 to 55%. The drying can be, for example, in a range from 2 to 15 days, more specifically in a range from 3 to 14 days, and more specifically in a range from 4 to 10 days. The drying is performed under light shielding and more preferably in a dark place. In the present disclosure, "light shielding" refers to preventing the plant from being irradiated with a PAR at a PPFD that is not lower than 3 times (more preferably not lower than twice) the light compensation point of the plant. The drying is preferably performed under sterilization, such as under ultraviolet irradiation.

The product produced by the manufacturing method of the present disclosure is, for example, a dried plant (including a part of the plant, which can be, for example, a dried spike and/or a dry leaf) or a cut piece, crushed piece, ground body, or powder of the plant. Specific examples of the dried plant include a dried cannabis, dried flower, dried fruit, dried peel, and potpourri.

The product containing the rare cannabinoid compound can itself be used as a medical cannabinoid (or medical cannabis or medical marijuana) (dried product) and can also be used as a raw material for manufacturing a pharmaceutical product containing the cannabinoid compound. On the other hand, the product containing the terpene compound can itself be used as a fragrance and can also be used as a raw material for manufacturing a functional food, essential oil, or perfume.

From another viewpoint, the present disclosure provides a method of manufacturing an extract containing a plant rare cannabinoid compound and/or a terpene compound, the method including extracting at least one rare cannabinoid compound or terpene compound from a plant treated by the method of treating a post-harvest plant described above.

The extract may be in the form of an oil or resin.

For the extraction, an entire plant or a part of the plant (e.g., a flower and/or leaf) may be used as long as the plant has been treated by the method of treating a post-harvest plant described above. The plant may be used as is for the extraction but may be used after cutting or crushing.

The extraction can be performed by any of known methods for extracting a cannabinoid compound or terpene compound from a plant. The method can be, for example, solvent extraction, supercritical extraction, or supercritical fluid extraction.

A solvent to be used for the solvent extraction can be appropriately selected from known organic solvents. Examples of the organic solvent include methanol, ethanol, n- or iso-propanol, butanol, acetonitrile, acetone, dioxane, ethyl acetate, diethyl ether, methyl-t-butyl ether, dimethyl sulfoxide, dimethylformamide, ethylene glycol, propylene glycol, glycerol, tetrahydrofuran, dichloromethane, trichloromethane, tetrachloromethane, chloroform, trichloroethylene, propane, butane, pentane, hexane, cyclohexane, heptane, octane, isooctane, toluene, and benzene. The organic solvent can be used alone or as a mixed solvent of two or more. The supercritical fluid extraction can be performed, for example, using $CO_2$ as a solvent. The extraction may be performed under stirring or shaking. In addition, the extraction may be performed under warming (e.g., in a range from 30 to 60° C.) and/or pressure. The extraction may be reflux extraction. The extraction time is not particularly limited, can be appropriately determined from the viewpoint of extraction efficiency, and is, for example, in a range from 5 minutes to 5 hours.

The solvent may be removed from the resulting extracted liquid, for example, by rotary evaporation. In addition, the resulting extracted liquid may be filtered through an appropriate filter or may be subjected to centrifugation, for example, to remove a contaminant.

The method for manufacturing an extract of the present disclosure may further include decarboxylation before the extraction. The decarboxylation converts a cannabinoid compound present in the acid form into the active form, and this can provide a highly active extract.

The decarboxylation can be performed by heating to a temperature, for example, in a range from 70 to 180° C., more specifically in a range from 80 to 170° C., more specifically in a range from 90 to 160° C., and more specifically in a range from 100 to 150° C., for example, for 5 minutes to 8 hours, more specifically for 10 minutes to 6 hours, more specifically for 15 minutes to 4 hours, and more specifically for 30 minutes to 2 hours.

In addition, the plant may be dried and/or frozen before the extraction, and if applicable, before the decarboxylation. The drying can be performed by any method, but the method can be, for example, hot air drying, ambient temperature drying, drying under reduced pressure, or freeze drying. The drying can be performed under the conditions described above for the method of manufacturing a product containing a plant rare cannabinoid compound and/or a terpene compound.

The extract containing the rare cannabinoid compound obtained as an oil by the above manufacturing method can itself be used as a medical cannabinoid (oil product) and can also be used as a raw material (e.g., plant drug substance) for manufacturing a pharmaceutical product containing the cannabinoid compound. On the other hand, the extract containing the terpene compound obtained by the above manufacturing method can itself be used as a fragrance and can also be used as a raw material for manufacturing a perfume containing the terpene compound. The resulting terpene compound-containing extract can also be used as an additive to the cannabinoid compound-containing extract with the expectation of the entourage effect.

From yet another viewpoint, the present disclosure provides a method of manufacturing a plant rare cannabinoid compound or terpene compound, the method including purifying a rare cannabinoid compound or a terpene compound from a plant treated by the method of treating a post-harvest plant described above.

The purification can be performed by chromatography using a preparative column, for example, flash chromatography, liquid chromatography (especially HPLC), thin-layer chromatography (especially TPTLC), or supercritical chromatography (SFC). Examples of the preparative column include a silica gel column (e.g., C18 and C8). The purification can also be performed by distillation (especially fractional distillation).

Examples of an eluent in the chromatography (e.g., gradient method) include those described above for the extraction, and more specifically, the eluent can be a mixed solvent of a nonpolar solvent and a polar solvent.

The rare cannabinoid compound obtained by the above manufacturing method can be used as a raw material (e.g., plant drug substance) for manufacturing a pharmaceutical product containing the cannabinoid compound. On the other hand, the terpene compound obtained by the above manufacturing method can be used as a raw material for manufacturing a fragrance or perfume.

The present disclosure also provides a plant treatment apparatus including:
- a holding unit configured to hold a harvested plant; and
- an irradiation unit configured to emit light having a peak wavelength in a wavelength range from 270 to 290 nm and light having a peak wavelength in a wavelength range from 370 to 400 nm,
- in which the irradiation unit can emit the light having a peak wavelength in the wavelength range from 270 to 290 nm and/or the light having a peak wavelength in the wavelength range from 370 to 400 nm toward a harvested plant held by the holding unit to irradiate the harvested plant.

The plant treatment apparatus of the present disclosure is suitable for implementing the method of treating a plant of the present disclosure described above.

Holding Unit

The holding unit is in any configuration which allows the holding unit to hold a post-harvest plant (entire plant body or its portion) and to place a site desirable for irradiation in the post-harvest plant held by the holding unit (the desired site to be irradiated may be the entire post-harvest plant held by the holding unit) to an irradiation area of the irradiation unit. An aspect in which the holding unit holds the plant is not particularly limited and can be, for example, placing, housing, clamping, or gripping. The holding unit is placed such that the holding unit can place, to the irradiation area of the irradiation unit, a site desirable for irradiation in the plant held by the holding unit at least temporarily (e.g., when the holding unit is in a predetermined position).

In some embodiments, the holding unit has a structure and size, which allow the placement of a plant on the unit. The placement surface of such a holding unit (placement unit) can be composed of, for example, at least a portion of: a top surface of a floor, shelf, or stand; or an inner bottom surface of a container, tray, or cage. The placement surface is not limited to one continuous surface but may be composed of a plurality of separated surfaces or may be a virtual surface, for example, a top surface of a mesh or grid panel. The shape of the placement unit is not particularly limited.

As a specific example, the placement surface is a belt upper surface of a belt conveyor in which the belt portion is in a mesh or net form. According to this specific example, the apparatus can irradiate the post-harvest plant placed on the upper surface of the belt from two directions, upward and downward, and thus can more efficiently achieve an increased amount of at least one rare cannabinoid compound and/or at least one terpene compound by the light irradiation of the present disclosure.

As another specific example, the placement surface is composed of a water-holding material. According to this specific example, the apparatus supplies the liquid containing water to the water-holding material, and this can easily and continuously supply the liquid to the post-harvest plant placed on the water-holding material and thus can maintain the post-harvest plant in a relatively fresh state. As a result, the amount of at least one rare cannabinoid compound and/or at least one terpene compound synthesized by the light irradiation of the present disclosure can be maintained in the plant, and thus this can more efficiently achieve an increased amount of at least one rare cannabinoid compound and/or at least one terpene compound.

The water-holding material is any material that can hold a liquid and can supply the liquid to a plant in contact with and is not particularly limited, and a water-holding material known in the art can be used. Specific examples of the water-holding material include nonwoven fabrics, sponges, and water absorbing-polymers. The liquid containing water can be supplied, for example, from a liquid supply unit described later.

In some other embodiments, the holding unit has a structure and size with which the unit can house a plant inside. The shape of such a holding unit (housing container) is not particularly limited. The housing container may also serve as a storage or storage container. In addition, the housing container may be stationary, or movable or transportable (e.g., a shipping container and a luggage compartment of a freight vehicle). This enables utilization of time during movement or transportation for treating the plant and thus can improve time efficiency. The housing container may include an atmosphere control mechanism for controlling the temperature and/or humidity of the interior atmosphere.

As a specific example, the holding unit is a structure configured to hold a post-harvest plant, which is a shoot system including a stem, or a stem and flower and/or leaf, in a substantially upright or inclined state and configured to hold a liquid at its bottom (e.g., a hollow rectangular parallelepiped or cylinder opened at one end and closed at the other end). According to this specific example, the apparatus can easily and/or continuously supply the liquid containing water to the post-harvest plant held on the holding unit and thus can maintain the plant in a relatively fresh state.

A material of the holding unit is usually not particularly limited, but there may be a case in which the holding unit is present on the optical path from the irradiation unit to a site desirable for irradiation of the plant held by the holding unit. For such a case, the material is preferably a material substantially transparent to the light having a peak wavelength in the wavelength range from 270 to 290 nm and/or the light having a peak wavelength in the wavelength range from 370 to 400 nm or a material having one or a plurality of openings that allow the light to pass through (e.g., mesh structure). Here, "substantially transparent" to a specific light refers to transmitting 50% or more of the light, for example, 60% or more, preferably 70% or more, more preferably 80% or more, and more preferably 90% or more. Thus, the holding unit can be configured, for example, with a mesh or grid placement surface and/or wall.

The holding unit may constitute a part of a conveying body configured to convey, to the irradiation area of the irradiation unit, a post-harvest plant held by the holding unit. This allows the plant treatment apparatus of the present disclosure to continuously treat a large amount of plants. In this case, the conveying body may be able to convey the post-harvest plant held by the holding unit to an injection area of a liquid injection unit (described later) and/or to a dark chamber (described later). The conveying body can be, for example, a mesh conveyor, a conveying stage, or a conveying robot.

The holding portion may be configured to include an upper surface of the conveying body, at least a part of which passes through the irradiation area of the irradiation unit and extends to the dark chamber.

As a specific example, the holding unit can hold the liquid containing water supplied from a liquid supply unit described later. According to this specific example, the apparatus can preserve the freshness of the plant held by the holding unit at least during the irradiation or in an irradiation chamber (described later), or suppress loss in the freshness. In the form in which the holding unit can hold a liquid together with the plant to the dark chamber described later, the apparatus can preserve the freshness of the plant or suppress a reduction in the freshness to the dark chamber, and in the form in which the holding unit can hold a liquid together with the plant to a drying chamber described later, the apparatus can preserve the freshness of the plant or suppress loss in the freshness to the drying chamber.

Irradiation Unit

The irradiation unit is configured to emit the light having a peak wavelength in the wavelength range from 270 to 290 nm and/or the light having a peak wavelength in the wavelength range from 370 to 400 nm toward a plant ("plant to be irradiated") held in a predetermined position by the holding unit to irradiate the plant.

The irradiation unit (more specifically, a light source of the irradiation unit) is placed such that the irradiation unit can emit the light to a site desirable for irradiation of the plant held by the holding unit at least temporarily (e.g., when the holding unit holds the plant to be irradiated in a predetermined position).

The irradiation unit may include an optical system including one or more optical system components known in the art, such as a lens, reflective mirror, optical filter, mask, or diffusion plate.

The irradiation unit may irradiate the plant to be irradiated from any direction (one direction or two or more directions) around the plant. The irradiation unit preferably irradiates the plant to be irradiated from two directions. Irradiation from two directions, especially from opposite directions (e.g., upward and downward directions, leftward and rightward directions, or forward and backward directions), enables efficient irradiation of the plant to be irradiated in a wider area.

The irradiation unit includes a light source configured to emit the light having a peak wavelength in the wavelength range from 270 to 290 nm and/or a light source configured to emit the light having a peak wavelength in the wavelength range from 370 to 400 nm.

In some embodiments, the irradiation unit includes a light source configured to emit the light having a peak wavelength in the wavelength range from 270 to 290 nm. In some other embodiments, the irradiation unit includes a light source configured to emit the light having a peak wavelength in the wavelength range from 370 to 400 nm.

In yet some other embodiments, the irradiation unit includes a light source configured to emit the light having a peak wavelength in the wavelength range from 270 to 290 nm and the light having a peak wavelength in the wavelength range from 370 to 400 nm. According to this embodiment, the irradiation unit can irradiate the same plant with the two types of light sequentially or simultaneously and thus can efficiently increase the amount of the rare cannabinoid compound and/or the terpene compound in the plant. In addition, the irradiation unit can also irradiate the plant with a more effective wavelength of light according to the type of the plant to be irradiated or according to the target rare cannabinoid compound and/or the target terpene compound. Thus, the irradiation unit can achieve an efficient increase in the amount according to the type of the plant to be irradiated and/or the target rare cannabinoid compound and/or the target terpene compound.

As a specific example, the irradiation unit includes:
a first light source configured to emit the light having a peak wavelength in the wavelength range from 270 to 290 nm,
a second light source configured to emit the light having a peak wavelength in the wavelength range from 370 to 400 nm, and
a control unit configured to control the first light source and the second light source,
in which the control unit is configured to control the first light source and the second light source, such that the irradiation unit is capable of emitting either the light having a peak wavelength in the wavelength range from 270 to 290 nm or the light having a peak wavelength in the wavelength range from 370 to 400 nm. The control unit may control turning on and off the first light source and the second light source.

In yet some other embodiments, the irradiation unit includes:
a light source configured to emit the light in the wavelength range from 270 to 290 nm and the light in the wavelength range from 370 to 400 nm simultaneously,
a first optical filter having a transmittance for the light in the wavelength range from 270 to 290 nm higher than a transmittance for light other than the light in the wavelength range from 270 to 290 nm,
a second optical filter having a transmittance for the light in the wavelength range from 370 to 400 nm higher than a transmittance for light other than the light in the wavelength range from 370 to 400 nm, an optical system configured to direct light emitted from the light source to the first optical filter and the second optical filter, and an optical system control unit configured to control the optical system to direct light emitted from the light source to either the first optical filter or the second optical filter.

From the viewpoint of efficiency, preferably, the irradiation unit does not emit light in a wavelength range from 410 to 700 nm or emits the light in the wavelength range from 410 to 700 nm at an irradiance of less than 20%, more specifically less than 10%, more specifically less than 5%, more specifically less than 2%, and more specifically less than 1% of an irradiance of the light having a peak wavelength in the wavelength range from 270 to 290 nm and/or the light having a peak wavelength in the wavelength range from 370 to 400 nm.

Thus, in some embodiments, a light source configured to emit the light having a peak wavelength in the wavelength range from 270 to 290 nm or a light source configured to emit the light having a peak wavelength in the wavelength range from 270 to 290 nm and the light having a peak wavelength in the wavelength range from 370 to 400 nm does not emit the light in the wavelength range from 410 to 700 nm or emits the light in the wavelength range from 410 to 700 nm at an irradiance of less than 20%, more specifically less than 10%, more specifically less than 5%, more specifically less than 2%, and more specifically less than 1% of an irradiance of each of the light having a peak wavelength in the wavelength range from 270 to 290 nm or the light having a peak wavelength in the wavelength range from 370 to 400 nm.

Alternatively or additionally, from the viewpoint of a negative effect on the plant, for example, cell damage, preferably, the irradiation unit does not emit light in a wavelength range from 200 to 260 nm or emits the light in the wavelength range from 200 to 260 nm at an irradiance of less than 20%, more specifically less than 10%, more specifically less than 5%, more specifically less than 2%, and more specifically less than 1% of an irradiance of the light having a peak wavelength in the wavelength range from 270 to 290 nm and/or the light having a peak wavelength in the wavelength range from 370 to 400 nm.

Thus, in some embodiments, a light source configured to emit the light having a peak wavelength in the wavelength range from 270 to 290 nm or a light source configured to emit the light having a peak wavelength in the wavelength range from 270 to 290 nm and the light having a peak wavelength in the wavelength range from 370 to 400 nm does not emit the light in the wavelength range from 200 to 260 nm or emits the light in the wavelength range from 200 to 260 nm at an irradiance of less than 20%, more specifically less than 10%, more specifically less than 5%, more specifically less than 2%, and more specifically less than 1% of an irradiance of each of the light having a peak wavelength in the wavelength range from 270 to 290 nm or the light having a peak wavelength in the wavelength range from 370 to 400 nm.

Examples of the light source of the irradiation unit can include light emitting diodes (LEDs) and laser diodes (LDs), as well as xenon lamps, fluorescent lamps, incandescent lamps, metal halide lamps, and high-pressure mercury lamps, which have a necessary optical filter. The irradiation unit may be configured with an array of light sources. The optical filter can be a filter having a transmittance for the light having a peak wavelength in the wavelength range from 270 to 290 nm higher than a transmittance for the light in the wavelength range from 410 to 700 nm and/or the light in the wavelength range from 200 to 260 nm. Alternatively or additionally, the optical filter can be a filter having a transmittance for the light having a peak wavelength in the wavelength range from 370 to 400 nm higher than a transmittance for the light in the wavelength range from 410 to 700 nm and/or the light in the wavelength range from 200 to 260 nm. The light source is particularly preferably a light emitting diode (LED) or a laser diode (LD). The irradiation unit using an LED or LD can easily achieve irradiation with the light in a wavelength useful to increase the amount of the rare cannabinoid compound and/or the terpene compound in the plant while avoiding irradiation with light in a wavelength that is not useful to increase the amount of the rare cannabinoid compound and/or the terpene compound in the plant or can be harmful to the plant. In addition, the use of an LED or LD is preferred also from the viewpoints of energy efficiency and economy due to energy aggregation, low heat generation, low power consumption, and long life. Additionally, the use of an LED or LD facilitates control or management of the illuminance or irradiance.

An LED or LD suitable as the light source configured to emit the light having a peak wavelength in the wavelength range from 270 to 290 nm is an LED or LD having a peak wavelength in the wavelength range from 270 to 290 nm, more specifically an LED or LD having a spectrum with a peak wavelength of 280±10 nm and a full width at half maximum in a range from 0.1 to 20 nm, more specifically in a range from 0.1 to 15 nm, more specifically in a range from 0.1 to 10 nm, and more specifically in a range from 0.1 to 5 nm, and more specifically an LED or LD having a spectrum with a peak wavelength of 280±5 nm and a full width at half maximum in a range from 0.1 to 20 nm, more specifically in a range from 0.1 to 15 nm, more specifically in a range from 0.1 to 10 nm, and more specifically in a range from 0.1 to 5 nm.

An LED or LD suitable as the light source configured to emit the light having a peak wavelength in the wavelength range from 370 to 400 nm is an LED or LD having a peak wavelength in the wavelength range from 370 to 400 nm, more specifically an LED or LD having a spectrum with a peak wavelength of 385±15 nm and a full width at half maximum in a range from 0.1 to 20 nm, more specifically in a range from 0.1 to 15 nm, more specifically in a range from 0.1 to 10 nm, and more specifically in a range from 0.1 to 5 nm, more specifically an LED or LD having a spectrum with a peak wavelength of 385±10 nm and a full width at half maximum in a range from 0.1 to 20 nm, more specifically in a range from 0.1 to 15 nm, more specifically in a range from 0.1 to 10 nm, and more specifically in a range from 0.1 to 5 nm, and more specifically an LED or LD having a spectrum with a peak wavelength of 385±5 nm and a full width at half maximum in a range from 0.1 to 20 nm, more specifically in a range from 0.1 to 15 nm, more specifically in a range from 0.1 to 10 nm, and more specifically in a range from 0.1 to 5 nm.

The LD or LED may be provided in the form of an array.

The irradiation area of the irradiation unit especially when not irradiated has a PPFD preferably of 10 $\mu mol/m^2/s$ or lower, more preferably of 5 $\mu mol/m^2/s$ or lower, more preferably of 2 $\mu mol/m^2/s$ or lower, and more preferably of 1 $\mu mol/m^2/s$ or lower. Thus, as one specific example, the irradiation unit is placed in an irradiation chamber which can shield photosynthetically active radiation from outside. According to this specific example, the apparatus can hold the plant in a dark place when not irradiating, thus can substantially prevent photosynthesis of the plant, and can avoid energy consumption due to photosynthesis or activation of other synthetic systems. As a result, this can more efficiently achieve the effect of increasing the amount associated with the irradiation by the apparatus of the present disclosure.

The irradiation unit (more specifically, the light source of the irradiation unit) may include a control unit for controlling the irradiation unit.

The control unit controls the dimming of the light source and/or the timing of turning on and off the light source.

The control unit may control which of continuous light, intermittent light, or a combination of these is emitted by the irradiation unit. For the irradiation unit configured to emit intermittent light, the control unit may control the pulse width and/or the duty ratio of the intermittent light.

The control unit can be, for example, a pulse width modulation circuit, or a pulse width modulation circuit and a timer, and may be constituted of, for example, a microcomputer, a relay, and/or a switching element.

Liquid Supply Unit

In some embodiments, a plant treatment apparatus of the present disclosure may further include a liquid supply unit.

The liquid supply unit is configured to be able to supply the liquid containing water to a plant held by the holding unit.

As a specific example, the liquid supply unit supplies the liquid containing water to the holding unit holding at least the stem of the plant. According to this specific example, the supplied liquid is absorbed into the plant through the stem (more specifically, the cross section formed at the time of harvest) held by the holding unit, and thus the apparatus can easily and/or effectively and/or efficiently achieve maintaining the freshness of the plant or suppressing a loss in the freshness of the plant.

The liquid supply unit may include a light source for irradiating the liquid containing water with ultraviolet light. According to this configuration, the ultraviolet irradiation can kill a microorganism, such as a bacterium, and/or a virus, which may be present in the liquid, and can prevent or suppress a microorganism or the like from entering into the plant. Thus, the apparatus with this configuration is suitable for obtaining or manufacturing the rare cannabinoid compound and/or the terpene compound for food or pharmaceuticals to be taken by humans or non-human animals, products or extracts containing the compound.

As a specific example, the liquid supply unit is a liquid jetting unit configured to be able to jet the liquid containing water toward a plant held by the holding unit. The jetting can be performed utilizing water pressure and/or air pressure. In a suitable specific example, a jetted area of the liquid jetting unit is arranged such that the jetted area is superimposed onto the irradiation area of the irradiation unit, and the irradiation unit emits the light toward the plant to irradiate the plant, in the liquid jetting atmosphere made by the liquid jetting unit. According to this suitable specific example, the apparatus can efficiently prevent or reduce the temperature increase of the plant being irradiated and thus enables longer continuous irradiation or intermittent irradiation at shorter intervals. As a result, the apparatus can efficiently increase the amount of the rare cannabinoid compound and/or the terpene compound.

Other Configurations

The plant treatment apparatus of the present disclosure can include a dark chamber which can shield photosynthetically active radiation from outside. As described above for the treatment method of the present disclosure, storing the plant irradiated with the light having a peak wavelength in the wavelength range from 270 to 290 nm and the light having a peak wavelength in the wavelength range from 370 to 400 nm in a dark place can further increase the amount of at least one rare cannabinoid compound and/or at least one terpene compound in the plant.

"A dark chamber which can shield photosynthetically active radiation from outside" means that when lighting that can be provided inside the dark chamber is turned off, the internal photosynthetically active photon flux density can be 10 $\mu mol/m^2/s$ or lower, more specifically 5 $\mu mol/m^2/s$ or lower, more specifically 2 $\mu mol/m^2/s$ or lower, and more specifically 1 $\mu mol/m^2/s$ or lower.

The dark chamber may be provided separately from the irradiation chamber having the irradiation unit inside. In a case in which the irradiation chamber can shield photosynthetically active radiation from outside, it can also serve as the dark chamber.

In a configuration where the dark chamber is provided separately from the irradiation chamber, the holding unit can play a role for conveying the plant from the irradiation chamber to the dark chamber.

The dark chamber may be provided with a cooler to store the plant at low temperature.

The plant treatment apparatus of the present disclosure can include a drying chamber which is configured to control the internal temperature and/or humidity and can shield photosynthetically active radiation from outside, in place of or in addition to the dark chamber. Drying the plant can suppress the degradation of the rare cannabinoid compound and/or the terpene compound increased in the plant and/or can suppress damage of the plant due to, for example, mold.

The drying chamber can maintain the chamber temperature, for example, at a temperature in a range from 15 to 35° C., more specifically at a temperature in a range from 18 to 30° C., and more specifically in a range from 20 to 27° C., and maintain the relative humidity, for example, at a humidity in a range from 20 to 70%, more specifically in a range from 25 to 65%, more specifically in a range from 30 to 60%, and more specifically in a range from 35 to 55%. For this purpose, the drying chamber may be provided with an air conditioner or a ventilator.

The plant treatment apparatus of the present disclosure may include a reflective member which can reflect the light having a peak wavelength in the wavelength range from 270 to 290 nm and/or the light having a peak wavelength in the wavelength range from 370 to 400 nm. The reflective member can be placed in a position relative to the irradiation unit and the plant to reflect the light once and/or twice or more to direct the light to the plant, the light being emitted from the irradiation unit and having a peak wavelength in the wavelength range from 270 to 290 nm and/or the light having a peak wavelength in the wavelength range from 370 to 400 nm. For example, in a configuration where the irradiation unit is provided to irradiate the plant from above the plant, the holding unit may include the reflective member at a lateral side and/or a lower side of the plant to irradiate the plant from the lateral side and/or the lower side. Alternatively, in a configuration in which the irradiation unit and the holding unit are placed within a housing, the reflective member can be provided on at least a portion of the inner surface of the housing, for example, on a surface of a lateral side and/or a lower side of the plant.

Thus, in a specific embodiment, the plant treatment apparatus of the present disclosure further includes:

an irradiation chamber including the irradiation unit inside; and a dark chamber which is configured to shield photosynthetically active radiation from outside,
in which the holding unit constitutes a part of a conveying body configured to convey the plant from the irradiation chamber to the dark chamber such that a site desirable for irradiation of the plant passes through an irradiation area irradiated by the irradiation unit in the irradiation chamber.

In a more specific embodiment, the plant treatment apparatus of the present disclosure further includes a drying chamber configured to control the internal temperature and/or humidity and to shield photosynthetically active radiation from outside, in which the holding unit constitutes a part of a conveying body configured to convey the plant from the irradiation chamber to the drying chamber through the dark chamber.

According to these embodiments, the apparatus can automate the treatment from the irradiation to the dark place storage, and further to the drying and thus can noticeably increase the efficiency of the treatment of the plant.

In a certain embodiment, the irradiation chamber and/or the dark chamber and/or the drying chamber further includes a germicidal lamp for indoor sterilization. According to this embodiment, the plant can be treated in a clean atmosphere, more specifically in a sterile atmosphere. Thus, the apparatus with this configuration is suitable for obtaining or manufacturing the rare cannabinoid compound and/or the terpene compound for food or pharmaceuticals which are taken by humans or non-human animals, or products or extracts containing the compound.

Figure 2:
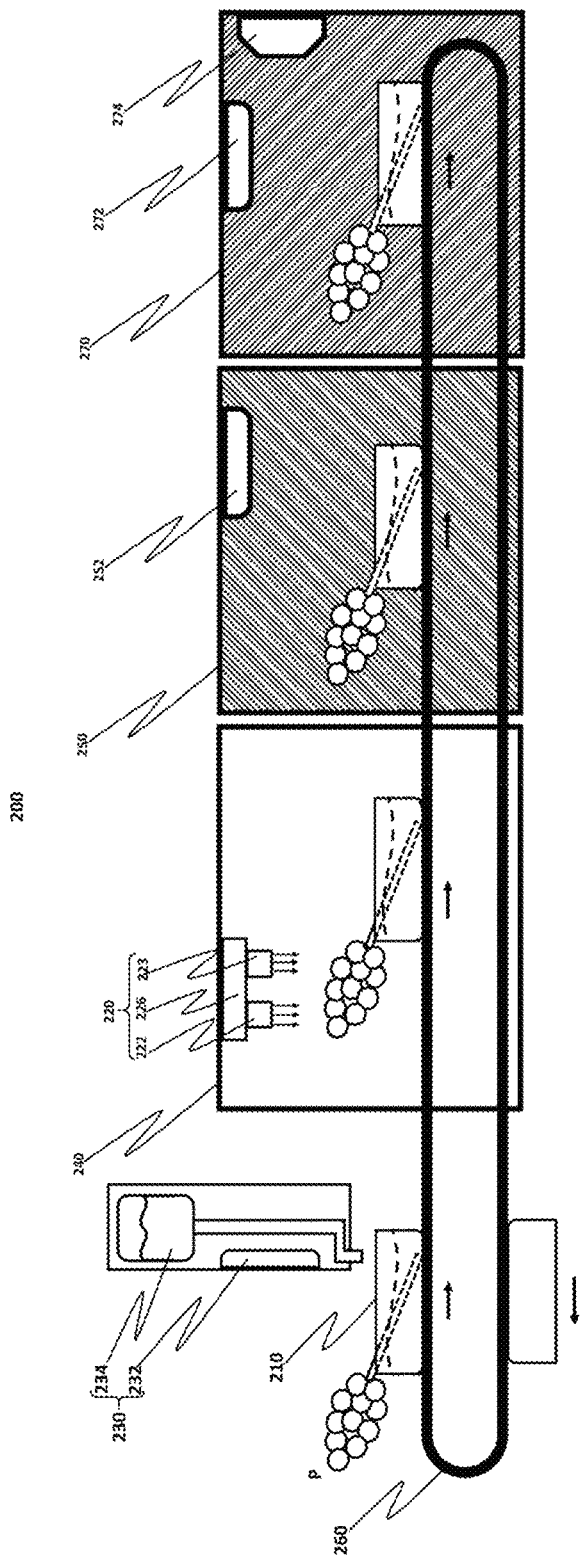
FIG. 2 is an exemplary schematic diagram illustrating another embodiment of an apparatus of the present disclosure.

The apparatus of the present disclosure will be described below with reference to schematic diagrams, FIGS. 1 and 2, illustrating specific examples of embodiments of the apparatus of the present disclosure.

Embodiment 1

A configuration 100 of the apparatus of the present disclosure schematically illustrated in FIG. 1 includes a holding unit 110 and an irradiation unit 120. The holding unit 110 and the irradiation unit 120 may be contained within a housing 180.

The holding unit 110 can hold a stem of a plant P. The holding unit 110 may be configured to hold the liquid containing water. The apparatus 100 may include a plurality of holding units 110.

The irradiation unit 120 includes a light source 122 configured to emit light having a peak wavelength in a wavelength range from 270 to 290 nm, a light source 123 configured to emit light having a peak wavelength in a wavelength range from 370 to 400 nm, and a control unit 126 configured to control the light sources 122 and 123. Thus, the irradiation unit 120 can emit the light having a peak wavelength in the wavelength range from 270 to 290 nm and/or the light having a peak wavelength in the wavelength range from 370 to 400 nm toward the plant P to irradiate the plant P. The light sources 122 and 123 may be in the form of a light source array, such as an LD array or LED array.

The housing 180 may be composed entirely of a light-shielding material. Alternatively, the housing 180 may be at least partially composed of a material substantially transparent to visible light (in a range from 400 to 800 nm) to allow the plant P to be visible from outside the housing.

The apparatus 100 may also be provided with a reflective member 182 which can reflect the light having a peak wavelength in the wavelength range from 270 to 290 nm and/or the light having a peak wavelength in the wavelength range from 370 to 400 nm. The reflective member 182 may be placed on at least a portion of an inner surface of the housing 180 or may be provided in the holding unit 110.

According to this embodiment, the apparatus 100 of the present disclosure can increase the amount of the rare cannabinoid compound and/or the terpene compound in a plant on display and/or during transportation.

Embodiment 2

A configuration 200 of the apparatus of the present disclosure schematically illustrated in FIG. 2 includes a holding unit 210 and an irradiation unit 220. The apparatus 200 further includes, as optional components, a liquid supply unit 230, an irradiation chamber 240, a dark chamber 250, a drying chamber 270, and a conveying body 260.

The holding unit 210 is configured to hold a stem of a plant P and is also configured to hold a liquid 234 containing water, which is supplied from the liquid supply unit 230. The apparatus 200 may include a plurality of holding units 210 as illustrated. The holding unit 210 may hold the liquid by simply a water storage or by a water-holding material.

The holding unit 210 may be conveyed by the conveying body 260 from the liquid supply position to the drying chamber 270 or may constitute a part of the conveying body 260 extending from the liquid supply position to the drying chamber 270.

The liquid supply unit 230 has a configuration which allows the liquid supply unit 230 to hold the liquid 234 containing water and to supply the liquid to the holding unit 210. The supply from the liquid supply unit 230 to the holding unit 210 is by pouring or spraying. The liquid supply unit 230 may include a light source for irradiating the liquid 234 containing water with ultraviolet light.

The irradiation unit 220 includes a light source 222 configured to emit light having a peak wavelength in a wavelength range from 270 to 290 nm, a light source 223 configured to emit light having a peak wavelength in a wavelength range from 370 to 400 nm, and a control unit 226 configured to control the light sources 222 and 223. Thus the irradiation unit 220 can emit the light having a peak wavelength in the wavelength range from 270 to 290 nm and/or the light having a peak wavelength in the wavelength range from 370 to 400 nm toward the plant P to irradiate the plant P. The light sources 222 and 223 may be in the form of a light source array, such as an LD array or LED array. The irradiation unit 220 may be provided within the irradiation chamber 240. In FIG. 2, the irradiation unit 220 is provided such that the irradiation unit 220 can irradiate from above the plant P. But the irradiation unit 220 may additionally or alternatively be placed such that the irradiation unit 220 can irradiate from a lateral side and/or lower side of the plant P. The irradiation chamber 240 preferably can shield photosynthetically active radiation from outside, but this is not essential.

The dark chamber 250 and the drying chamber 270 are shielded from photosynthetically active radiation from outside. The dark chamber 250 and the drying chamber 270 may further include germicidal lamps 252 and 272 for indoor sterilization.

The drying chamber 270 includes an air conditioner 274 configured to control the internal temperature and/or humidity. The drying chamber 270 may include a ventilator in place of the air conditioner. The drying chamber 270 including the air conditioner 274 can also serve as the dark chamber 250.

Although not shown, the irradiation unit 220 and/or the dark chamber 250 may include a cooler configured to maintain the internal temperature at low temperature.

This embodiment is suitable for continuous treatment and/or automated treatment of a plant and/or treatment of a plant under sterilization.

As an example of use of the present disclosure, the apparatus can be used for lighting, such as store lighting, showcase lighting, food storage lighting, and downlighting. In using the apparatus in a store, a plant, such as a vegetable, fruit, or flower, on display in the store or/and stored in a warehouse is UV-irradiated under the conditions of the present disclosure after the end of business hours and stored after the UV irradiation until the start of business hours, and this can increase the amount of a useful component in the plant by the business hours. In using the apparatus at home, a plant, such as a vegetable or fruit stored in a food storage or a fresh flower arranged in a vase, is UV-irradiated under the conditions of the present disclosure at bedtime, and this can increase the amount of a useful component in the plant by the wake-up time.

A logistics container may be equipped with an apparatus for UV irradiation under the conditions of the present disclosure. UV irradiation and dark place storage during transportation of a plant can increase the amount of a useful component in the plant by the time of delivery of the goods.

A street light may be equipped with an apparatus for UV irradiation under the conditions of the present disclosure.

For example, in a case in which a plant is present near a street light, such as a flower bed or a park, UV-irradiating the flower for about 15 minutes to 3 hours after sunset and then turning off the light allows the same effect as that of the dark place storage and can increase the amount of a useful component, such as a fragrance component, by the next morning.

EXAMPLES

Experiment 1

Gene Expression Analysis in *Arabidopsis thaliana*

*Arabidopsis thaliana* was irradiated with LED light (peak wavelength: 280 nm; full width at half maximum: 10 nm) with an illuminance of 2.5 µmol/m²/s for 45 minutes (irradiance 6750 µmol/m²).

Immediately after the irradiation, the shoot was frozen in liquid nitrogen. Then, NucreoSpin (trade name) RNA plant (available from Takara Bio Inc.) was used according to the instruction manual, and a total RNA was prepared.

RNA-seq analysis was performed on the total RNA prepared (Takara Bio Inc.). A NovaSeq 6000 system (available from Illumina, Inc.) was used for the sequence analysis. The analysis was performed on three samples per experimental group.

As a result, irradiation with light having a peak wavelength near 280 nm increased a gene (AT2G47460) involved in the flavonol synthesis process by threefold or more (334%).

This gene AT2G47460 corresponds to a gene CAN738 involved in synthesis processes of a cannabinoid compound and terpene compound in plants of the genus *Cannabis*. Thus, the above result suggests that, in genus *Cannabis*, irradiation with light having a peak wavelength near 280 nm can stimulate the synthesis processes of the cannabinoid compound and terpene compound.

Experiment 2

The following experiment was conducted in Israel.

Three cultivars of the plant of the genus *Cannabis* (*C. sativa* L.), BLK Label, RGM Argvana Heart, and MUN Shine 6, were grown in a plant factory under the following control conditions.

Room temperature: in a range from 22 to 23° C.
Low-pressure sodium lamp
Photosynthetically active photon flux density: 200 µmol/m²/s
Long-day conditions: light period/dark period=16 hours/8 hours Component ratios of THC and CBD in the flower after drying of the species are as shown in the table below; BLK Label is classified as a high THC strain, RGM Argvana Heart as a THC-CBD balanced strain, and MUN Shine 6 as a high CBD strain.

TABLE 1

| Species name | Ministry of Agriculture and Rural Development of Israel submission No. | Component percentage | Type |
| --- | --- | --- | --- |
| BLK Label | 4851/19 | THC > 15%, CBD < 1% | High THC strain |
| RGM Argvana Heart | 4839/19 | THC ≈ 7 %, CBD ≈ 7% | THC-CBD balanced strain |
| MUN Shine 6 | 4841/19 | THC < 1 %, CBD > 15% | High CBD Strain |

Flowers were collected from the plants of the genus *Cannabis* after a duration range from about 40 to about 60 days from seeding. Upon collection, flowers of similar color and similar size were selected to reduce variations in component content between individuals.

The flower collected from each strain was irradiated with LED light having a peak wavelength of 280 nm and a full width at half maximum of 10 nm (hereinafter referred to simply as "280-nm light") or LED light having a peak wavelength of 385 nm and a full width at half maximum of 11 nm (hereinafter referred to simply as "385-nm light") under the following conditions. NCSU334B and NVSU233B (available from Nichia Corporation) were used as light sources for the 280-nm light and the 385-nm light, respectively. The plant was irradiated from directly above, and reflective surfaces of aluminum foil were placed around four sides of the plant to be irradiated.

TABLE 2

| Irradiation condition name | Irradiation light (wavelength) | Illuminance | Irradiation time | Irradiance |
| --- | --- | --- | --- | --- |
| Cont. | Not irradiated | — | — | 0 |
| UVA15 min | 385 nm | 150 µmol/m²/s | 15 min | 135,000 µmol/m² |

TABLE 2-continued

| Irradiation condition name | Irradiation light (wavelength) | Illuminance | Irradiation time | Irradiance |
|---|---|---|---|---|
| UVA60 min | 385 nm | 150 µmol/m$^2$/s | 60 min | 540,000 µmol/m$^2$ |
| UVA180 min | 385 nm | 150 µmol/m$^2$/s | 180 min | 1,620,000 µmol/m$^2$ |
| UVB15 min | 280 nm | 5 µmol/m$^2$/s | 15 min | 4,500 µmol/m$^2$ |
| UVB60 min | 280 nm | 5 µmol/m$^2$/s | 60 min | 18,000 µmol/m$^2$ |
| UVB180 min | 280 nm | 5 µmol/m$^2$/s | 180 min | 54,000 µmol/m$^2$ |

Four collected flowers were used as one sample, and four samples were prepared for each condition. That is, a total of 16 flowers were prepared for each strain.

Light-irradiated samples were transferred to a dark place at a temperature of about 25° C. and a relative humidity in a range from about 20% to about 70% within 5 minutes after light irradiation to store for one week and then dried. Non-irradiated samples were transferred to the same condition dark place as described above within three hours after harvest to store and then dried. The samples after drying were placed in a bag and sealed, and stored until analysis.

Cannabinoid compounds and terpene compounds contained in the flowers after drying were analyzed. Analyses were performed by ultra-high performance high separation liquid chromatography (UPLC) for major cannabinoid compounds, liquid chromatography/mass spectrometry (LC/MS) for rare cannabinoid compounds, and by gas chromatography/mass spectrometry (GC/MS) for terpene compounds (CannaSoul Analytics, Israel).

Results 1

Figure 3:
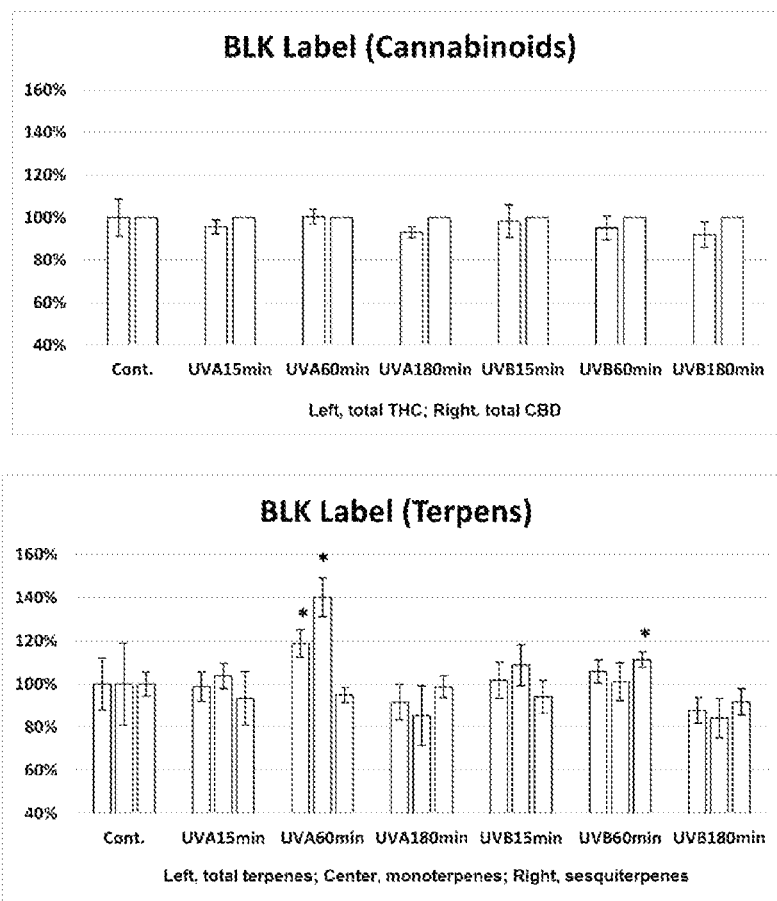
FIG. 3 is a graph showing changes in contents of total THC, total CBD, and monoterpenes, sesquiterpenes, and total terpene compounds in a post-harvest plant of the genus Cannabis BLK Label by light irradiation according to an exemplary method of the present disclosure.
Figure 4:
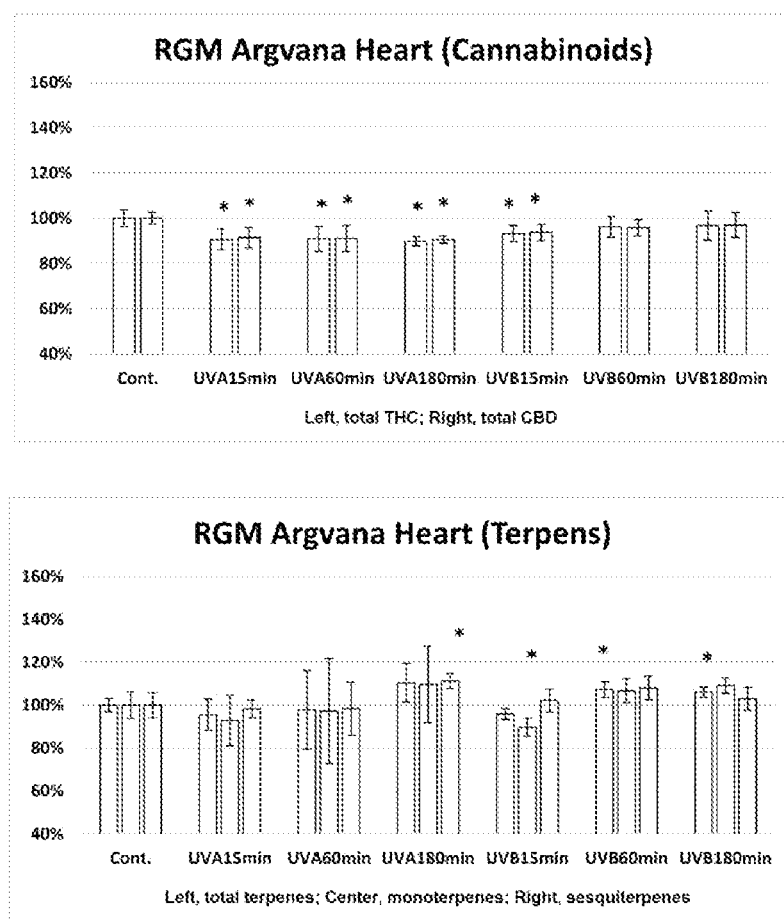
FIG. 4 is a graph showing changes in contents of total THC, total CBD, and monoterpenes, sesquiterpenes, and total terpene compounds in a post-harvest plant of the genus Cannabis RGM Argvana Heart by light irradiation according to an exemplary method of the present disclosure.
Figure 5:
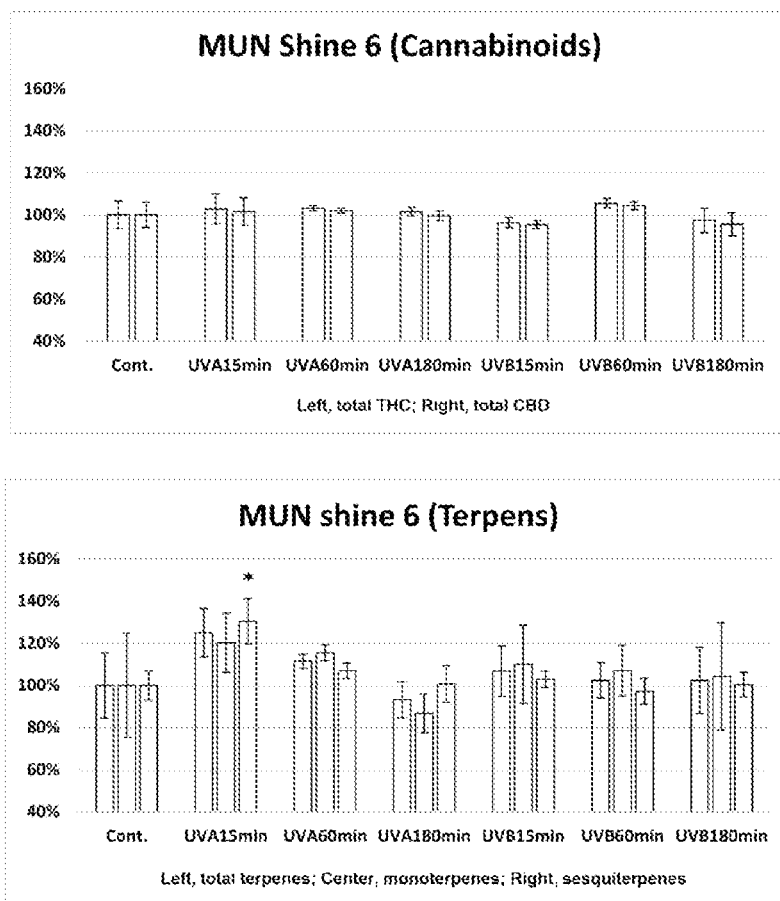
FIG. 5 is a graph showing changes in contents of total THC, total CBD, and monoterpenes, sesquiterpenes, and total terpene compounds in a post-harvest plant of the genus Cannabis MUN Shine 6 by light irradiation according to an exemplary method of the present disclosure.
Figure 6:
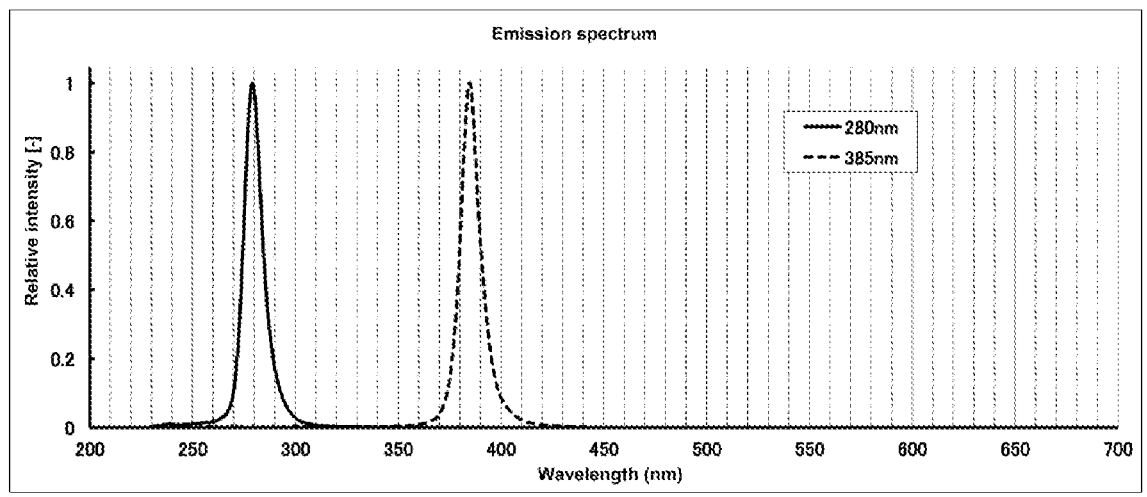
FIG. 6 is a diagram showing an exemplary spectrum of a light source used in an experiment of the present disclosure.

Changes in the content of total THC, total CBD, and monoterpenes, sesquiterpenes, and total terpene compounds are shown in FIGS. 3 to 5 for each strain. The change in the content is indicated by determining the content in the irradiated sample as a percentage relative to the content (100%) in the non-irradiated sample (Cont.). The total THC content means the total of THC content and THCA content, the total CBD content means the total of CBD content and CBDA content, and the total terpene content means the total of content of monoterpenes and content of sesquiterpenes.

In FIGS. 3 to 5, the asterisk "*" indicates that the content changed noticeably (p≤0.05; t-test) in the irradiated samples (n=4) relative to the non-irradiated samples (n=4).

For the total THC content and total CBD content, no change due to the light irradiation was noted in BLK Label (high THC strain) and MUN Shine 6 (high CBD strain); on the other hand, in RGM Argvana Heart (balanced strain), reductions of a little less than 10% due to the irradiation with the 280-nm light (at all irradiation times) and the irradiation with the 385-nm light for short time (15 minutes) were observed.

For the total content of terpenes, an increase in the amount was noted in BLK Label (high THC strain) and RGM Argvana Heart (balanced strain) with both light irradiations although the effective irradiance was different; on the other hand, in MUN Shine 6 (high CBD strain), an increase in the amount due to the irradiation with the 280-nm light for short time (15 minutes) was noted.

Thus, in the plant of the genus *Cannabis*, irradiation with the 280-nm light and/or the 385-nm light was found to increase the total terpene compound content.

Results 2

For the samples in which a noticeable increase in the amount of the terpene compound was observed, the components that had increased in amount were analyzed and the results are shown in Tables 3 to 5 below. Components that had noticeably increased in content (p≤0.05; t-test) in the irradiated samples (n=4) relative to those in the non-irradiated samples (n=4) are shown. The values in the tables are percentages of increase calculated by the following equation: (average value of irradiated sample)/(average value of non-irradiated sample)×100(%).

TABLE 3

Species: BLK Label

| Irradiation conditions | UVA60 min | | UVB60 min | |
|---|---|---|---|---|
| Components whose amount increased | (-)-b-Myr-cene | 166% | Linalool | 114% |
| | cis-Ocimene | 151% | trans-b-Far-nesene | 114% |
| | D/L-Limo-nene | 142% | D/L-Borneol | 112% |
| | Nerol | 128% | b-Caryo-phyllene | 112% |
| | Terpinolene | 124% | a-Humulene | 111% |
| | a-Pinene | 116% | a-Terpineol | 110% |
| | b-Pinene | 114% | | |

TABLE 4

Species: RGM Argvana Heart

| Irradiation conditions | UVA180 min | | UVB60 min | | UVB180 min | |
|---|---|---|---|---|---|---|
| | Caryophyllene oxide | 130% | cis-Ocimene | 121% | cis-Ocimene | 124% |
| | trans-Nerolidol | 127% | trans-Nerolidol | 110% | (-)-b-Myrcene | 115% |
| | (-)-Guaiol | 115% | (-)-Guaiol | 109% | trans-Nerolidol | 111% |
| | (-)a-Bisabo-lol | 111% | (-)a-Bisabolol | 109% | (-)a-Bisabolol | 111% |
| | trans-b-Farnesene | 110% | | | trans-b-Farnesene | 108% |
| | Valencene | 110% | | | | |

TABLE 5

Species: MUN Shine 6

| Irradiation conditions | UVA15 min | |
|---|---|---|
| Components whose amount increased | (-)-Guaiol | 137% |
| | (-)a-Bisabo-lol | 134% |
| | Linalool | 133% |
| | a-Humulene | 130% |
| | trans-Nerolidol | 129% |

TABLE 5-continued

Species: MUN Shine 6

| Irradiation conditions | UVA15 min | |
|---|---|---|
| | b-Caryophyllene | 129% |
| | D/L-Borneol | 128% |
| | a-Terpineol | 128% |
| | Fenchol | 127% |
| | (+)-Ledene | 126% |

In the plant of the genus *Cannabis*, irradiation with the 280-nm light and/or the 385-nm light was found to increase the amounts of the monoterpene compounds and the sesquiterpene compounds.

These terpene compounds have an entourage effect with THC and/or CBD in addition to their individual pharmacological effects and are useful components of medical *cannabis*.

Results 3

For all the samples, components of the rare cannabinoid compounds that had increased in amount were analyzed, and the results are shown in Tables 6 to 8 below. Components that had noticeably increased in content ($p \leq 0.05$; t-test) in the irradiated samples (n=4) relative to those in the non-irradiated samples (n=4) are shown. The values in the tables are percentages of increase calculated by the following equation: (average value of irradiated sample)/(average value of non-irradiated sample)×100(%).

TABLE 6

Species: BLK Label

| Irradiation conditions | UVA60 min | | UVB60 min | |
|---|---|---|---|---|
| Components whose amount increased | THC-C4 | 126% | THC-C4 | 129% |

TABLE 7

Species: RGN Argvana Heart

| Irradiation conditions | UVA15 min | | UVA180 min | |
|---|---|---|---|---|
| Components whose amount increased | CBT-3 | 201% | CBNDA | 127% |
| | CBNDA | 165% | | |
| | CBTA-3 | 159% | | |
| | CBTA-1 | 140% | | |
| | CBD-C4 | 132% | | |

| Irradiation conditions | UVA15 min | | UVB60 min | | UVB180 min | |
|---|---|---|---|---|---|---|
| Components whose amount increased | CBT-3 | 208% | CBG-C6 | 543% | CBGA-C6 | 115% |
| | CBEVA | 177% | THC-C4 | 187% | CBDA-C7 | 107% |
| | CBNDA | 172% | CBD-C4 | 140% | | |
| | CBTA-3 | 168% | CBGA-C4 | 117% | | |
| | CBD-C4 | 147% | Sesqui-CBG | 114% | | |
| | CBTA-1 | 144% | CBDA-C7 | 114% | | |
| | CBT-1 | 136% | CBCVA | 112% | | |
| | CBNVA | 118% | Cannaflavin B | 106% | | |

TABLE 8

Species: MUN Shine 6

| Irradiation conditions | UVA180 min | |
|---|---|---|
| Components whose amount increased | CBEA | 116% |
| | CBNDA | 137% |

In the plant of the genus *Cannabis*, irradiation with the 280-nm light and/or the 385-nm light was found to increase the amounts of the rare cannabinoid compounds.

These rare cannabinoid compounds have an entourage effect with THC and/or CBD and are useful components of medical *cannabis*, and a new pharmacological effect is also expected.

Experiment 3

Roses (cut flowers), *Narcissus tazetta* var. *chinensis* (cut flowers), *Citrus unshiu* (fruits), lemons (fruits), and phak chi, all of which were grown outdoors, were purchased.

At the time of purchase, roses and *Narcissus tazetta* var. *chinensis* were kept in water, and *Citrus unshiu*, lemons, and phak chi were stored under refrigeration.

The harvested plants were irradiated with 280-nm light or 385-nm light under the following conditions. LEDs NCSU334B and NVSU233B (available from Nichia Corporation) were used as light sources for the 280-nm light and the 385-nm light, respectively.

For each plant, individuals of similar color and similar size were selected to reduce variations in component content between individuals.

The roses and *Narcissus tazetta* var. *chinensis* were laid in trays and irradiated with light while water was supplied to the cut surface of the stem using a capillary phenomenon.

TABLE 9

| Irradiation condition name | Irradiation light (wavelength) | Illuminance | Irradiation time | Irradiance |
|---|---|---|---|---|
| Cont. | Not irradiated | — | — | 0 |
| UVA30 min | 385 nm | 150 µmol/m²/s | 30 min | 270,000 µmol/m² |
| UVB30 min | 280 nm | 5 µmol/m²/s | 30 min | 9,000 µmol/m² |

The *Citrus unshiu* and the lemons were irradiated with light with the pericarp still attached.

TABLE 10

| Irradiation condition name | Irradiation light (wavelength) | Illuminance | Irradiation time | Irradiance |
|---|---|---|---|---|
| Cont. | Not irradiated | — | — | 0 |
| UVA30 min | 385 nm | 150 µmol/m²/s | 30 min | 270,000 µmol/m² |
| UVB30 min | 280 nm | 5 µmol/m²/s | 30 min | 9,000 µmol/m² |

The phak chi was placed in a tray filled with water and was irradiated with light while the cut surface of the stem was immersed in water.

TABLE 11

| Irradiation condition name | Irradiation light (wavelength) | Illuminance | Irradiation time | Irradiance |
|---|---|---|---|---|
| Cont. | Not irradiated | — | — | 0 |
| UVA15 min | 385 nm | 150 μmol/m²/s | 15 min | 135,000 μmol/m² |
| UVB15 min | 280 nm | 5 μmol/m²/s | 15 min | 4,500 μmol/m² |

The plants were all irradiated from directly above, and reflective surfaces of aluminum foil were placed around four sides of the plant to be irradiated.

Each light-irradiated plant was transferred to a dark place at a temperature of about 25° C. and a relative humidity of about 20% to about 70% within 5 minutes after light irradiation to store for two days. Non-irradiated plants were transferred to a dark place under the same conditions as described above after obtained.

The roses and Narcissus tazetta var. chinensis were stored with the cut surface of the stem immersed in water, the Citrus unshiu and lemons were packed in plastic bags having a plurality of holes and stored, and the phak chi was stored in the same state as that during the light irradiation.

After stored in a dark place, only flowers for roses and Narcissus tazetta var. chinensis, only pericarps for Citrus unshiu and lemons, and phak chi as is were frozen in liquid nitrogen.

The frozen samples were then crushed using a mortar and pestle, then placed in a plastic bag, and stored at −70° C.

The change in the content of terpene compounds in each plant was analyzed by GC-MS.

For the analysis, 10 flowers of the rose and 25 flowers of Narcissus tazetta var. chinensis respectively were used as one sample, pericarps of six fruits of Citrus unshiu and pericarps of seven lemons respectively were used as one sample, and about 50 g of phak chi was used as one sample, and one sample was prepared for each condition.

The frozen storage sample was thawed and then pretreated as follows. The thawed sample underwent extraction by adding sodium sulfate and BHT-containing methanol, then hexane was added, and the mixture was shaken and then centrifuged, and the hexane phase was recovered. The recovered hexane phase was subjected to GC-MS under the following conditions. Cannabis Terpene Mix B (available from Sigma-Aldrich Co. LLC) was used as the standard material.

GC Conditions:

Injection port temperature: 250° C.

Injection mode: splitless

Analytical column: InertCap Pure-WAX (film thickness 0.25 μm, inner diameter 0.25 mm×length 30 m)

Temperature increasing conditions: from 45° C. (maintaining for 2 min), increased at 10° C./min to 140° C. (maintaining for 0.5 min), then increased at 30° C./min to 250° C. (maintaining for 8 min)

Carrier flow rate: 1 mL/min

MS Conditions

Ion source temperature: 220° C.

Ionization method: EI

Ionization energy: 70 eV

Measurement mode: SIM

Monitoring ion

The following monitoring ions were employed to detect each compound.

TABLE 12

| Compound name | Monitoring ion (m/z) |
|---|---|
| beta-Pinene | 93 |
| beta-Caryophyllene | 133 |
| Phytol | 71 |
| Limonene | 68 |
| Geraniol | 69 |
| (1S)-(−)-Camphor | 95 |
| Terpinolene | 121 |
| beta-Eudesmol | 59 |
| (+)-Borneol | 95 |
| (1S)-(+)-3-Carene | 161 |
| (−)-alpha-Terpineol | 59 |
| (1S)-(+)-3-Carene | 93 |
| Linalool | 121 |
| p-Cymene | 119 |

Results

For all the samples, components of the terpene compounds that had increased in amount were analyzed, and the results are shown in Tables 13 to 17 below. Components that had noticeably increased in content ($p \leq 0.05$; t-test) in the irradiated samples relative to those in the non-irradiated samples are shown. The values in the tables are percentages of increase calculated by the following equation: (value of irradiated sample)/(value of non-irradiated sample)×100 (%).

TABLE 13

| | Rose | | | |
|---|---|---|---|---|
| Irradiation conditions | UVA30 min | | UVB30 min | |
| Components whose amount increased | Geraniol | 329% | Geraniol | 336% |

TABLE 14

| | Narcissus tazetta var. chinensis | | | |
|---|---|---|---|---|
| Irradiation conditions | UVA30 min | | UVB30 min | |
| Components whose amount increased | Phytol | 117% | Phytol | 147% |

TABLE 15

| | Citrus unshiu | | | |
|---|---|---|---|---|
| Irradiation conditions | UVA30 min | | UVB30 min | |
| Components whose amount increased | (−)-alpha-Terpineol | 191% | (−)-alpha-Terpineol | 174% |
| | Linalool | 160% | Linalool | 137% |
| | Phytol | 107% | Phytol | 127% |

TABLE 16

Lemon

| Irradiation conditions | UVA30 min | | UVB30 min | |
|---|---|---|---|---|
| Components whose amount increased | Terpinolene | 142% | beta-Caryophyllene | 138% |
| | (-)-alpha-Terpineol | 139% | (-)-alpha-Terpineol | 138% |
| | beta-Pinene | 137% | (1S)-(-)-Camphor | 136% |
| | (1S)-(-)-Camphor | 132% | Geraniol | 135% |
| | beta-Caryophyllene | 131% | Terpinolene | 124% |
| | | | beta-Pinene | 118% |

TABLE 17

Phak chi

| Irradiation conditions | UVA30 min | |
|---|---|---|
| Components whose amount increased | Limonene | 230% |
| | beta-Pinene | 146% |
| | Terpinolene | 139% |
| | (+)-Borneol | 138% |
| | beta-Eudesmol | 126% |

Also in the various plant species belonging to families significantly different from that of the plant of the genus *Cannabis*, irradiation with the 280-nm light and/or the 385-nm light was found to increase the amounts of the terpene compounds (monoterpene, sesquiterpene, and diterpene compounds).

These components are used as raw materials for pharmaceuticals, functional foods, and perfumes, and as industrial raw materials.

Summarizing the results above leads to the understanding that irradiation with the light having a peak wavelength in the wavelength range from 270 to 290 nm and/or the light having a peak wavelength in the wavelength range from 370 to 400 nm can increase the amount of at least one rare cannabinoid compound and/or at least one terpene compound in the plant after harvest, and this effect is not limited to a particular family, genus, or species.

The reason for the increase in the amount of the rare cannabinoid compounds and/or the terpene compounds in the plants after harvest by irradiation with the light having a peak wavelength in the wavelength range from 270 to 290 nm and/or the light having a peak wavelength in the wavelength range from 370 to 400 nm is presumably that plant hormones (e.g., ethylene, jasmonic acid, or abscisic acid) and/or systemin acted to promote the syntheses of the cannabinoid compounds and/or the terpene compounds due to light stimulation.

In addition, the dark place storage of plants after the light irradiation inhibits photosynthesis, and thus (i) this presumably enables amino acids to be preferentially used for the syntheses of the cannabinoid compounds and/or the terpene compounds; and also (ii) cellular respiration in place of photosynthesis generates active oxygen, and as a result, this presumably further promotes the syntheses of the cannabinoid compounds and/or the terpene compounds.

The method and apparatus of the present disclosure are considered useful for plant stem cells, which are often used in cosmetics in recent years, also for medicinal herbs, edible flowers, chips of fragrant wood, seaweeds, such as microalgae and *Ulva prolifera*, and mushrooms.

What is claimed is:

1. A method of treating a post-harvest plant, the method comprising,
    irradiating a harvested plant with light having a peak wavelength in a wavelength range from 270 to 290 nm and/or light having a peak wavelength in a wavelength range from 370 to 400 nm at an irradiance effective to increase an amount of at least one rare cannabinoid compound and/or at least one terpene compound in the harvested plant,
    wherein an irradiance of light of all wavelengths in a wavelength range from 410 to 700 nm received by the harvested plant during the irradiating is less than 20% of the irradiance of the light having a peak wavelength in the wavelength range from 270 to 290 nm and/or less than 20% of the irradiance of the light having a peak wavelength in the wavelength range from 370 to 400 nm.

2. The method of treating a post-harvest plant according to claim 1, wherein the harvested plant is irradiated with the light having a peak wavelength in the wavelength range from 270 to 290 nm at an irradiance in a range from 2250 to 54000 µmol/m² and/or irradiated with the light having a peak wavelength in the wavelength range from 370 to 400 nm at an irradiance in a range from 33750 to 1620000 µmol/m².

3. The method of treating a post-harvest plant according to claim 1, wherein the harvested plant is within 12 hours after harvest.

4. The method of treating a post-harvest plant according to claim 1, wherein the harvested plant is freshly preserved at a time of the irradiating.

5. The method of treating a post-harvest plant according to claim 1, further comprising storing the harvested plant in a dark place for 12 hours or longer immediately after the irradiating.

6. The method of treating a post-harvest plant according to claim 1, wherein the harvested plant is a high THC strain or a THC-CBD balanced strain of harvested plants of the genus *Cannabis*, and the harvested plant is irradiated with the light having a peak wavelength in the wavelength range from 270 to 290 nm at an irradiance in a range from 9000 to 27000 µmol/m².

7. The method of treating a post-harvest plant according to claim 1, wherein the harvested plant is a high THC strain of harvested plants of the genus *Cannabis*, and the harvested plant is irradiated with the light having a peak wavelength in the wavelength range from 370 to 400 nm at an irradiance in a range from 270000 to 810000 µmol/m².

8. The method of treating a post-harvest plant according to claim 1, wherein the harvested plant is a high CBD strain of harvested plants of the genus *Cannabis*, and the harvested plant is irradiated with the light having a peak wavelength in the wavelength range from 370 to 400 nm at an irradiance in a range from 67000 to 210000 µmol/m².

9. The method of treating a post-harvest plant according to claim 1, wherein in the irradiating, the harvested plant is supplied with a liquid comprising water.

10. The method of treating a post-harvest plant according to claim 1, wherein
    the light having a peak wavelength in the wavelength range from 270 to 290 nm has a peak wavelength of 280±5 nm and a full width at half maximum in a range from 0.1 nm to 10 nm, and the light having a peak wavelength in the wavelength range from 370 to 400 nm has a peak wavelength of 385±5 nm and a full width at half maximum in a range from 0.1 nm to 10 nm.

11. The method of treating a post-harvest plant according to claim 1, where the rare cannabinoid compound is one or more compounds selected from the group consisting of tetrahydrocannabinol-C4 (THC-C4), cannabitriol-3 (CBT-3), cannabinodiolic acid (CBNDA), cannabitriolic acid-3 (CBTA-3), cannabitriolic acid-1 (CBTA-1), cannabidiol-4 (CBD-4), cannabielsovarinic acid (CBEVA), cannabitriol-1 (CBT-1), cannabivarinic acid (CBNVA), cannabigerol-C6 (CBG-C6), cannabigerolic acid-C4 (CBGA-C4), sesquicannabigerol (Sesqui-CBG), cannabidiolic acid-C7 (CBDA-C7), cannabichromevarinic acid (CBCVA), cannabigerolic acid-C6 (CBGA-C6), and cannabielsoinic acid (CBEA); and the terpene compound is one or more compound selected from the group consisting of β-myrcene, ocimene, linalool, limonene, nerol, terpinolene, α-pinene, β-pinene, α-terpineol, borneol, fenchol, guaiol, α-bisabolol, α-humulene, β-farnesene, β-caryophyllene, caryophyllene oxide, nerolidol, valencene, phytol, geraniol, camphor, β-eudesmol, and ledene.

12. A method of manufacturing a product comprising at least one rare cannabinoid compound and/or at least one terpene compound, the method comprising drying a product made by the method of claim 1.

13. A method of manufacturing an extract comprising at least rare cannabinoid compound or at least one terpene compound, the method comprising extracting the at least one rare cannabinoid compound or the at least one terpene compound from a product made by the method of claim 1.

14. A method of manufacturing a rare cannabinoid compound or a terpene compound, the method comprising purifying the rare cannabinoid compound or the terpene compound from a product made by the method described in claim 1.

15. A plant treatment apparatus comprising:
a holding unit configured to hold a harvested plant; and
an irradiation unit configured to emit light having a peak wavelength in a wavelength range from 270 to 290 nm and light having a peak wavelength in a wavelength range from 370 to 400 nm,
wherein the irradiation unit is configured to emit the light having the peak wavelength in the wavelength range from 270 to 290 nm and/or the light having the peak wavelength in the wavelength range from 370 to 400 nm toward a harvested plant held by the holding unit to irradiate the harvested plant.

16. The apparatus according to claim 15, further comprising a liquid supply unit configured to supply a liquid comprising water to the holding unit.

17. The apparatus according to claim 16, wherein the liquid supply unit comprises a light source configured to irradiate the liquid with ultraviolet light.

18. The apparatus according to claim 16, further comprising:
an irradiation chamber comprising the irradiation unit inside; and
a dark chamber configured to shield photosynthetically active radiation from outside,
wherein the holding unit constitutes a part of a conveying body configured to convey the harvested plant from the irradiation chamber to the dark chamber such that a site suitable for irradiation of the harvested plant passes through an area irradiated by the irradiation unit in the irradiation chamber.

19. The apparatus according to claim 18, wherein the holding unit is configured to hold the liquid together with the harvested plant from the irradiation chamber to the dark chamber.

20. The apparatus according to claim 18, further comprising a drying chamber configured to control an internal temperature and/or an internal humidity and configured to shield the photosynthetically active radiation from outside,
wherein the holding unit constitutes a part of a conveying body configured to convey the harvested plant from the irradiation chamber to the drying chamber through the dark chamber.

* * * * *